United States Patent [19]
Webb, II et al.

[11] Patent Number: 5,650,510
[45] Date of Patent: Jul. 22, 1997

[54] ANTIVIRAL PHOSPHONOMETHOXYALKYLENE PURINE AND PYRIMIDINE DERIVATIVES

[75] Inventors: Robert W. Webb, II, Guilford; Joanne J. Bronson, Madison; John C. Martin, Cheshire, all of Conn.

[73] Assignees: Institute of Organic Chemistry and Biochemistry of the Academy of Sciences of the Czech Republic, Czech Rep.; Rega Stichting v.z.w., Belgium

[21] Appl. No.: 829,784

[22] Filed: Jan. 31, 1992

Related U.S. Application Data

[63] Continuation of Ser. No. 249,809, Sep. 27, 1988, abandoned, which is a continuation-in-part of Ser. No. 114,340, Nov. 4, 1987, abandoned, which is a continuation-in-part of Ser. No. 932,112, Nov. 18, 1986, abandoned.

[51] Int. Cl.$^6$ ........................ A61K 31/675; C07F 9/6512
[52] U.S. Cl. .......................... 544/244; 544/243; 558/45; 558/124; 558/179; 558/189
[58] Field of Search ................. 514/81, 86; 544/243, 544/244

[56] References Cited

U.S. PATENT DOCUMENTS

| | | | |
|---|---|---|---|
| 4,287,188 | 9/1981 | Schaeffer | 514/81 |
| 4,590,269 | 5/1986 | Prisbe et al. | 544/276 |
| 4,605,658 | 8/1986 | Holy et al. | 514/261 |
| 4,659,825 | 4/1987 | Holy et al. | 544/244 |
| 4,670,424 | 6/1987 | MacCoss et al. | 514/81 |
| 4,724,233 | 2/1988 | De Clercq et al. | 514/81 |
| 4,808,716 | 2/1989 | Holy et al. | 544/244 |
| 5,142,051 | 8/1992 | Holy | 544/243 |

FOREIGN PATENT DOCUMENTS

| | | | |
|---|---|---|---|
| 0205826 | 12/1986 | European Pat. Off. | |
| 0206459 | 12/1986 | European Pat. Off. | 544/244 |
| 2134907 | 1/1984 | United Kingdom | |
| 84/00737 | 5/1984 | WIPO | |

OTHER PUBLICATIONS

Prisbe, et al., J. Med. Chem, vol. 29, pp. 671–675 (Mar. 17, 1986).
DeClercq, et al., Nature, vol. 323, pp. 464–467 (Apr. 10, 1986).
Holy, et al., Nucleic Acids Research, Symposium Series No. 14, pp. 277–278, (Apr. 11, 1984).
Baba, et al., Chemical Abstracts, vol. 106: 149011u (1987).
Steitwieser, Jr. "Introduction to Organic Chemistry" (2nd Edition) (MacMillan Publishing Co, 1981) pp. 132–134.
Balzarini, Antimicrob Agents & Chemotherapy, 37, 332(1993).
Chemistry of Nucleosides & Nucleotides vol. 1, pp. 215–216 (1988) Townsend, Ed.
Naesens, Antiv. Res. 16, 53 (1991).
Chu, J Het Chem 23, 287 (1986).
Yang, Antiviral Res Suppliment 1, Apr. 1991, p. 131.
Valenkamp et al. Ant. Microb. Agents & Chemotherapy 39(3), 746–749 (1995).
De clerq, J Med Chem 22(5), 510 (1979).
De clerq, Antiviral Res 8, 261 (1987).
Cohen, John, "New Drug Shows Promise in Monkeys," Science 270:1121–1122 (Nov. 17, 1995).
Holy et al., "Antiviral Acyclic Nucleotide Analogues," Antibiotics and Antiviral Compounds 455–462 (1993).
Tsai et al., "Prevention of SIV Infection in Macaques by (R)-9-(2-Phosphonylmethoxypropyl)adenine," Science 270:1197–1199 (Nov. 17, 1995).
Yu et al., "Synthesis and Antiviral Activity of 2'-Substituted 9-[2-(Phosphonomethoxy)ethyl]guanine Analogues," J Med Chem 36:2726–2738 (1993).
Balzarini et al, "Differential Antiherpesvirus and Antiretrovirus Effects of the (S) and (R) Enantiomers of Acyclic Nucleoside Phosphonates: Potent and Selective In Vitro and In Vivo Antiretrovirus Activities of (R)-9-(2-Phosphonomethoxypropyl)-2,6-Diaminopurine", Antimicrobial Agents and Chemotherapy, vol. 37, No. 2, pp. 332–338. (1993).
Birnbaum et al, "Conformation features of acyclonucleosides: structure of acyclovir, an antiherpes agent", Can. J. Chem., vol. 62, 1984, pp. 2646–2652.
De Clercq, "Broad–Spectrum Anti–DNA Virus and Anti–Retrovirus Activity of Phosphonylmethoxyalkylpurines and –Pyrimidines", Biochemical Pharmacology, vol. 42, No. 5 pp. 963–972, 1991.
Holy et al, "Phosphonylmethyl Ethers of Nucleosides and Their Acyclic Analogues", 1989 American Chemical Society, Chapter 4, pp. 51–71.
Keller et al, "Enzymatic Phosphorylation of Acyclic Nucleoside Analogs and Correlations with Antiherpetic Activities", Biochemical Pharmacology, vol. 30, No. 22, pp. 3071–3077, 1981.
Kim et al, "Acyclic Purine Phosphonate Analogues as Antiviral Agents. Synthesis and Structure—Activity Relationships", Journal of Medicinal Chemistry, 1990, vol. 33, No. 4, pp. 1207–1213.
Kritsyn et al, "Izvestiya Akademiya Nauk SSSR, Sertya Khimichaskaya" 8: 1846–1850 (1975).
Pauwels et al, "Phosphonylmethoxyethyl Purine Derivatives, A New Class of Anti–Human Immunodeficiency Virus Agents", Antimicrobial Agents and Chemotherapy, Jul. 1988, pp. 1025–1030.

*Primary Examiner*—Mark L. Berch
*Attorney, Agent, or Firm*—Max D. Hensley

[57] ABSTRACT

A series of compounds of Formula I which have anti-tumor activity, and are useful in treating viral infections, their compositions and use.

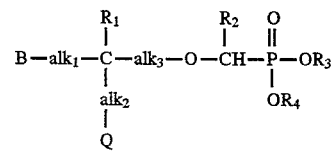

In Formula I B is a purine or pyrimidine base; $alk_1$ $alk_2$ and $alk_3$ are chemical bonds or alkylene groups; Q is hydrogen or hydroxyl; and $R_1$–$R_4$ are hydrogen or alkyl.

11 Claims, No Drawings

ANTIVIRAL PHOSPHONOMETHOXYALKYLENE PURINE AND PYRIMIDINE DERIVATIVES

CROSS REFERENCE TO RELATED APPLICATION

This application is a continuation of U.S. Ser. No. 249,809 filed Sep. 27, 1988, ABN which is a continuation-in-part of U.S. Ser. No. 114,340 filed Nov. 4, 1987 now abandoned, which is a continuation-in-part of Ser. No. 932,112 filed Nov. 18, 1986 now abandoned.

FIELD OF THE INVENTION

This invention concerns nucleotide analogs and their compositions and use. In particular it concerns acyclic phosphonomethoxyalkylene derivatives of purine and pyrimidine bases.

BACKGROUND OF THE INVENTION

Infectious viral diseases are recognized as an important medical problem. Progress against infectious viral diseases requires the development of drugs with selective antiviral activity while remaining benign to normal cell lines. A number of antiviral agents currently under study which seem to possess some selectivity, are nucleoside analogs. In general, these compounds are structural analogs of the naturally occurring nucleosides. Structural modification in either the purine or pyrimidine base nucleus and/or the saccharide component results in a synthetically modified nucleoside derivative which, when incorporated into a viral nucleic acid forming process, acts to disrupt further synthesis of viral nucleic acid. Effectiveness of these antiviral agents depends on selective conversion by viral enzymes, but not by host enzymes, to the corresponding nucleotide analog which is then converted to the triphosphate and incorporation into vital nucleic acid occurs. A problem with this antiviral strategy has been the emergence of certain viral strains whose enzymes poorly promote phosphorylation of the nucleoside analogs. To circumvent this problem, intact nucleotide analogs appear to be potentially quite useful as antivirals for incorporation into viral nucleic acid.

Reist and Sturm in WO84/04748, published Dec. 6, 1984, disclosed new phosphonic acid analogs of nucleoside phosphates which are useful as antivirals for incorporation into viral DNA. The structural formula for these compounds is shown below as 1.

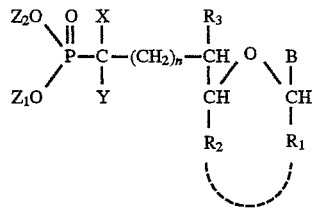

In the Reist compounds, B is a purine or pyrimidine base: $R_1$ and $R_2$ together complete a β-pentofuranose sugar or $R_1$ is H and $R_2$ is H or hydroxymethyl; $R_3$ is H or OH: X is H, OH or together with Y is carbonyl oxygen and Y can also be H; $Z_1$ and $Z_2$ are H or alkyl. These art compounds are generally distinguished from the compounds of the instant invention by 1) the ether-oxygen link to the carbon atom attached to the base which is intended to preserve or mimic the acetal oxygen bond of a pentofuranose sugar ring; and 2) the phosphate modification is a phosphonoalkylene moiety. In contrast, the acyclic sugar analog component of the instant compounds is comprised of an all carbon atom backbone up to a phosphonomethoxy moiety.

Similarly, synthesis and anti-Herpes-Virus activity of phosphate and phosphonate derivatives of 9-[(1,3-dihydroxy-2-propoxy)methyl]guanine (Formula 2) was disclosed by Prisbe, et al., in J. Med. Chem., 1986, 29, 671.

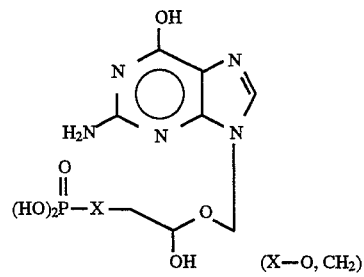

More closely related are adenine phosphonic acid analogs (Formula 3) and their syntheses which were disclosed in the UK Patent Application of Holy, et al., GB 2, 134, 907A published Aug. 22, 1984.

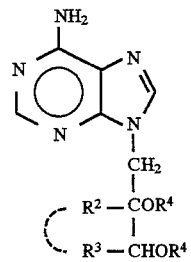

In formula 3, $R_2$ and $R_3$ are H or together complete a ribonucleoside ring; and both $R_4$ are alternately a hydrogen and —$CH_2P(O)(OH)_2$ group.

A preferred example of one of these compounds, known as (S)-HPMPA (Formula 4) was disclosed by DeClercq, et al., in Nature, 1986, 323, pp. 464–467 and earlier by Holy, et al., Nucleic Acids Research, Symposium Series No. 14, 1984 pp. 277–278. In our hands,(S)-HPMPA is only slightly active in mice inoculated with Herpes simplex virus- 2. In a 21 day protocol 30% of a group of animals treated i.p. with 50 mg/kg/day of(S)-HPMPA survived.

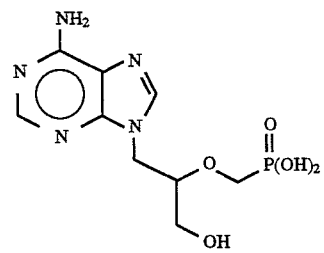

There is no teaching contained in these references, or a suggested combination thereof, which would make obvious the compounds, compositions, and use involved in the present invention.

SUMMARY OF THE INVENTION

Phosphonomethoxyalkylene purine and pyrimidine derivatives have been synthesized and found to possess useful antitumor, and antiviral activity. These compounds differ from the natural nucleotides by having structural variations in their sugar analog component which can be accompanied by variation in their nucleotide base moiety also. Additionally these compounds differ from the naturally occurring phosphate structure of nucleotides by nature of the oxygen-carbon-phosphorous bonds in these phosphonomethoxy derivatives. The compounds of this invention are represented by structural formula I.

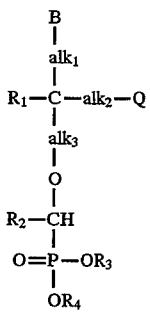

wherein B is a purine or pyrimidine base; $alk_1$, $alk_2$ and $alk_3$ are chemical bonds or alkylene groups; Q is hydrogen or hydroxyl; and $R_1$–$R_4$ are hydrogen or alkyl. Other aspects of this invention involve preparation of these compounds, their formulation into pharmaceutical compositions and the use of these formulations to treat viral infections, and tumors.

DETAILED DESCRIPTION OF THE INVENTION

The compounds comprising this invention are phosphonomethoxyalkylene purine and pyrimidine derivatives which have structural formula I.

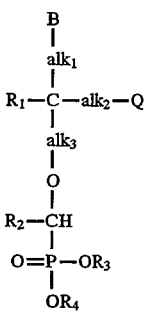

In structural Formula I, B is a purine or pyrimidine base selected from the group consisting of xanthine, hypoxanthine, guanine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, cytosine, 5-ethylcytosine, 5-methylcytosine, thymine, uracil, 5-bromouracil, 5-ethyluracil, 5-iodouracil, 5-propyluracil, 5-vinyluracil, and 5-bromovinyluracil. The symbols $alk_1$, $alk_2$ and $alk_3$ are independently selected from a chemical bond and alkylene chains containing 1 to 4 carbon atoms which may be straight-chain or branched. The symbol Q is hydrogen or hydroxyl. $R_1$ and $R_2$ are independently selected from hydrogen and $C_{1-4}$ alkyl and $R_3$ and $R_4$ are independently selected from hydrogen, $C_{1-6}$ alkyl, phenyl, and phenyl-$C_{1-4}$-alkylene. Compounds of the instant invention also include the corresponding salts, which may be base salts of the phosphonic acid moiety or an acid addition salt of the heterocyclic base; in addition to the zwitterionic forms and/or solvates of compounds of Formula I.

It is intended to exclude the 9-adenyl derivatives of Formulas 3 and 4 above which have been disclosed by Holy, et al., and DeClerq, et al. loc. cit. The latter also discloses the compound of Formula 5 which is referred to as PMEA, and is also excluded. The esters of the acids of Formulas 3, 4, and 5 are, however, part of the present invention. In our hands, PMEA has very low activity in mice against *Herpes simplex* virus 2. Only 30% of PMEA treated mice survived a 21 test period when treated i.p. with 200 mg/kg/day of PMEA. Higher doses are toxic.

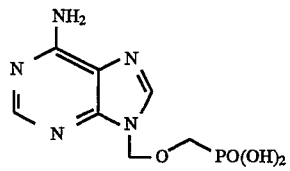

Those compounds of Formula I, therefore, are included in the invention wherein B is 9-adenyl and the other groups are as described wherein $alk_1$ and $alk_3$ together contain 2 to 8 carbon atoms and those compounds wherein one of $alk_1$ and $alk_3$ is methylene and the other is a chemical bond, and $alk_2$ is $C_{2-4}$ alkylene. The present invention also includes those compounds of Formula I wherein B is 9-adenyl, $alk_1$, $alk_2$, $alk_3$, $R_1$, $R_2$, and Q have the definitions given for the other bases B, and at least one of $R_3$ and $R_4$ is $C_{1-6}$ alkyl, phenyl, or phenyl-$C_{1-4}$-alkylene.

The compounds of the present invention can exist as optical isomers and both racemic and diastereomeric mixtures of these isomers which may exist for certain compounds as well as the individual optical isomers which are all within the scope of the present invention. While the racemic mixtures can be separated into their individual isomers through well-known techniques such as, for example, the separation of diastereomeric salts formed with optically active adjuncts, e.g. acids or bases followed by conversion back to the optically active substrates; in most instances, for compounds of the present invention, the preferred optical isomer can be synthesized by means of stereospecific reactions, beginning with the appropriate stereoisomer of the desired starting material. As indicated, the present invention also pertains to the pharmaceutically acceptable non-toxic salts of these compounds. Such salts may include those derived by combination of appropriate cations such as alkali and alkaline earth metal ions or ammonium and quaternary amino ions with the acid anion moiety of the phosphonic acid group. In addition salts may be formed from acid addition of certain organic and inorganic acids with basic centers of the purine, specifically guanine, or pyrimidine base. Finally it is to be understood that compounds of the present invention in their un-ionized as well as zwitterionic form and/or in the form of solvates are also considered part of the present invention.

Compounds of the present invention also exist in subclasses: two broad subclasses being those wherein B is either a purine or a pyrimidine base. Of these broad sub-classes there are preferred classes wherein the purine base is a guanine or a substituted guanine moiety and where the pyrimidine bases are either thymine or cytosine. The most preferred class of compounds is that wherein B is guanine or substituted guanine.

Preferred classes of sugar analog components, e.g.

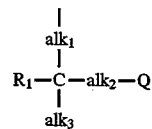

are those wherein $alk_2$ is a chemical bond and Q is hydrogen and those wherein $alk_2$ is methylene and Q is hydroxyl.

Compounds of the present invention may also be subclassed according to the structure of the phosphonate moiety. These classes are comprised of the diester, the monoester, and the diacid. Preferred subclasses of the phosphonate moiety are the monoester and the diacid.

The compounds of this invention can be prepared by the following two general procedures. The compounds wherein Q is hydrogen and $alk_2$ is a chemical bond can be generally prepared by Synthetic Scheme I and those compounds wherein Q is hydroxyl can generally be prepared from Synthetic Scheme II.

Synthetic Scheme I

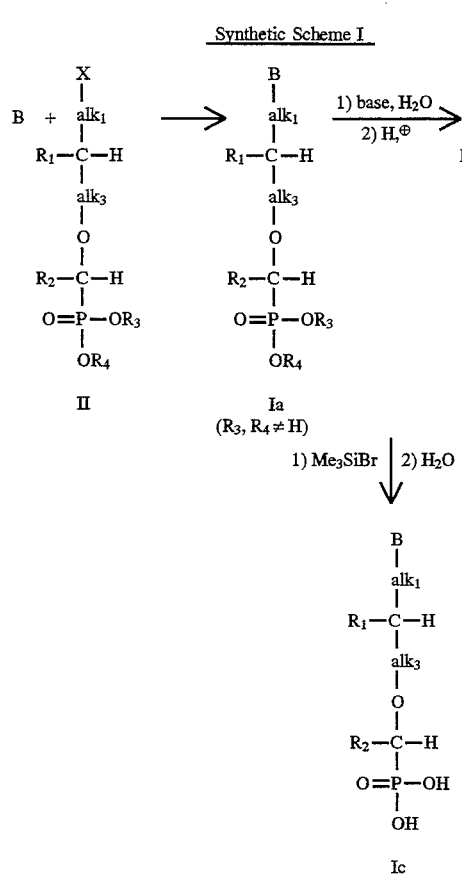

II
Ia ($R_3$, $R_4 \neq H$)
Ib ($R_3 \neq H$)
Ic

In Scheme I, B, $alk_1$, $alk_3$, $R_1$, $R_2$, $R_3$, and $R_4$ are as defined herein above. The symbol X represents a standard organic synthetic leaving group moiety such as chloride, bromide, iodide, tosylate, mesylate, triflate and the like. It is understood that in Scheme I, $alk_2$ is a chemical bond and Q is hydrogen. In the sequence of reactions comprising Scheme I the base B is converted to an anion by treatment with a base, such as an alkali metal hydride, in a non-reactive solvent, such as dimethylformamide (DMF), by stirring together for about 1 to 3 hours while in the temperature range of from room temperature to about 130°. The base anion is alkylated with a phosphonate diester intermediate of Formula II to give the diester product of Formula Ia. This diester may be converted either to the monoester, Ib or the diacid, Ic.

The conversion of the diester Ia to the monoester Ib can be accomplished either by dissolving Ia in aqueous hydroxide solution and holding at a temp between room temperature and 80° for about 1 to 6 hrs. Alternatively, when the base has an acid-labile protecting group on a reactive ring moiety of the base, the conversion of Ia to Ib, with concomitant removal of the protecting group, proceeds by dissolving the protected Ia compound in dilute acid, such as HCl, and holding in the temperature range from about room temperature to about 100° for about 1 to 6 hours.

The conversion of the diester Ia to the diacid Ic is readily accomplished by treating a solution of Ia, in a non-reactive solvent such as DMF, with excess trimethylsilyl bromide and stirring at about room temperature for about 4 to 6 hours. Volatiles are removed by concentration in vacuo to a residual material which is treated with water to generate the desired diacid product Ic.

In Synthetic Scheme II, shown below, Q is hydroxy.

Synthetic Scheme II

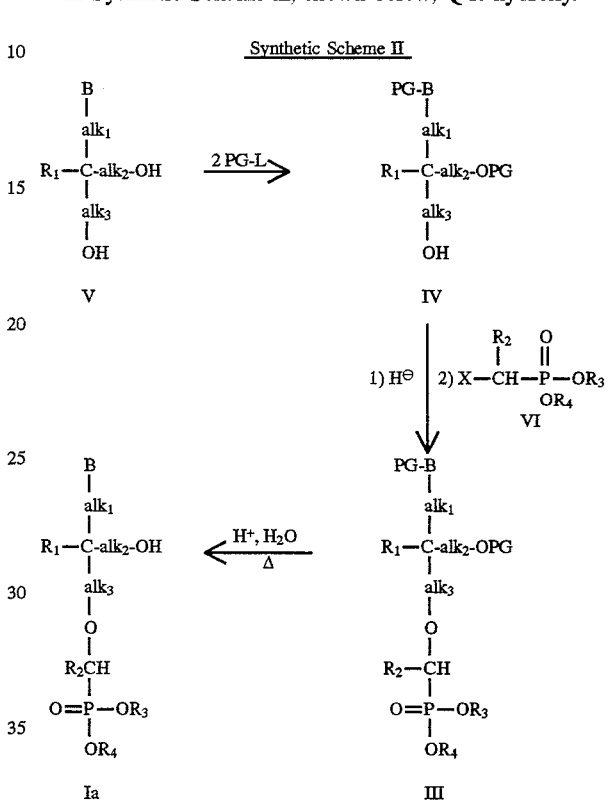

V
IV
Ia
III

It should also be apparent to one skilled in the art that compounds of Formula I wherein Q is hydroxy can also be made in some instances by the Scheme I process. An example of such a synthesis is shown below as Scheme III.

Scheme III

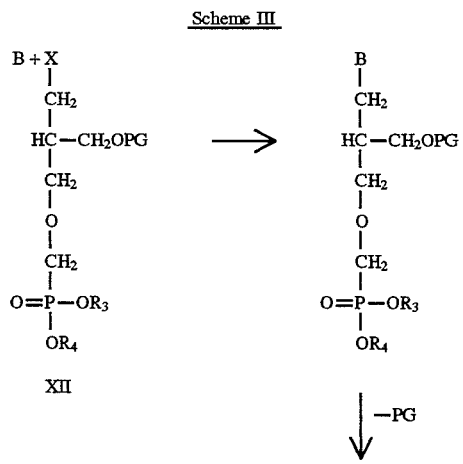

XII

-continued
Scheme III

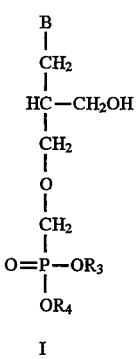

An advantage in using the process of Schemes I and III resides in the versatility of using intermediates of Formula II and XII; these may be coupled with a desired base selected from among a large group of such bases to give a variety of Formula I compounds in only one to three steps.

In the foregoing Scheme II B, $alk_1$, $alk_2$, $alk_3$, $R_1$, $R_2$, $R_3$, and $R_4$, are the same as defined hereinabove. The symbol PG represents an organic synthetic protecting group with preferred protecting groups belonging to the triphenylmethyl class of protecting groups. The symbol L is a synthetic organic leaving group which can be selected from the group defined for Synthetic Scheme I with halide preferred and chloride most preferred. In Synthetic Scheme II, $alk_3$ is either a chemical bond or is identical to $alk_2$. Scheme II comprises protecting the amino group moiety of the purine or pyrimidine base or the hydroxy moiety of the pyrimidine base as well as the terminal hydroxy group attached to $alk_2$. In general, this protecting group introduction reaction is carried out in reaction-inert solvents usually containing an excess of a basic reagent such as triethylamine whose function is to scavenge the leaving group anion and hydrogen ion which are liberated as the reaction proceeds. The resulting di-protected intermediate compound of Formula IV is treated with a metal hydride, e.g. NaH, followed by reaction with a phosphonate diester intermediate of Formula VI to give intermediate III. Removal of the protecting groups from intermediate III, done by either heating III in acidic media or by means of mild hydrogenolysis, results in the desired diester product Ia. It should also be obvious to one skilled in the art that this Ia product wherein Q is OH could be converted to a corresponding compound wherein Q=H by conversion of the hydroxy group to a leaving group (as by treatment with tosyl chloride or mesyl chloride) followed by hydride reduction to a branched alkyl product of Formula Ia wherein $alk_2$ is $C_{1-4}$ alkylene and Q is H.

The reaction intermediates of Formula II, V, and VI which were utilized in Synthetic Schemes I and II, are either commercially available or can be readily synthesized. Representative syntheses of these intermediates are given below in Schemes IV and V.

Scheme IV
Intermediate Compound Synthesis

Intermediate Compounds of Formula II

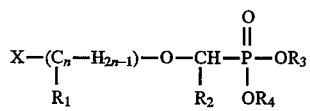

wherein

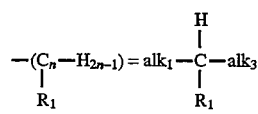

a) n = 2

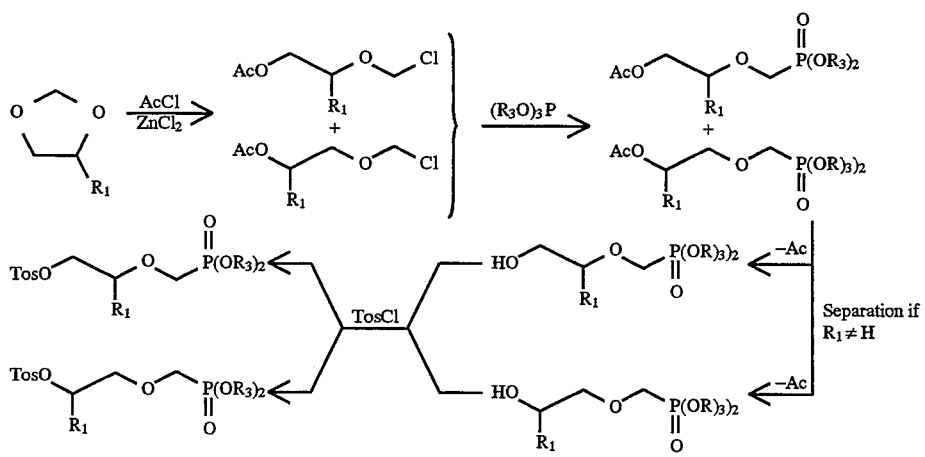

-continued
Scheme IV
Intermediate Compound Synthesis
b) n = 3,4
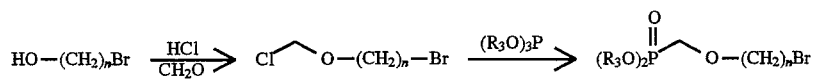
c) n = 5–7
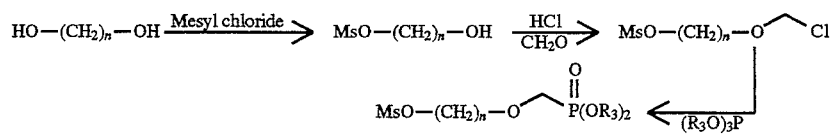
d) $R_2 \neq H$
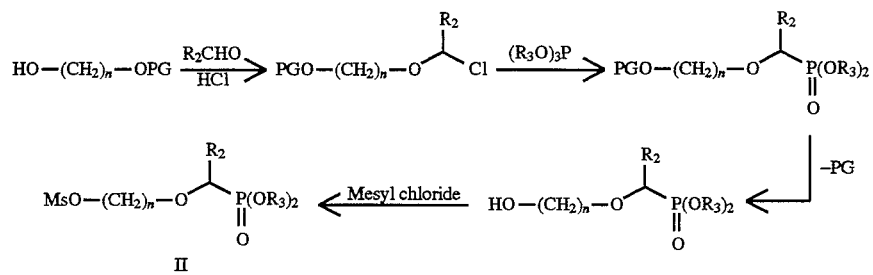
Intermediate Compounds of Formula XII
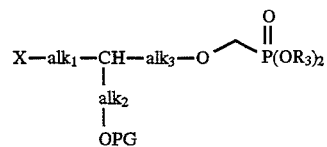
XII
A representative synthesis:
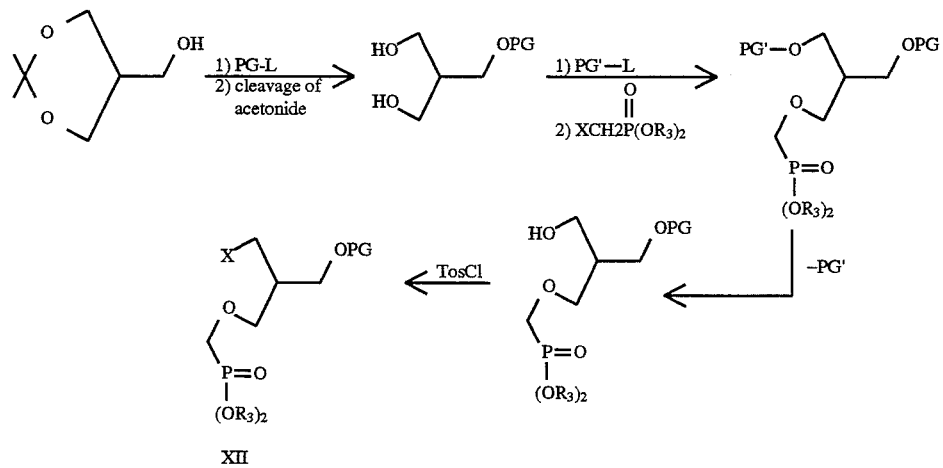
XII In Scheme IV, n is an integer from 1 to 7 and all other symbols are as previously defined or are conventional, e.g. Ac=acetyl=

etc. Reactions wherein a terminal hydroxy group is to be converted to a leaving group, e.g. —OH→—OTos, should be understood to be only representative as other sulfonate leaving group moieties, e.g. mesylate, triflate, can be used in place of tosylate or the -OH functionality can be converted to other types of leaving groups, e.g. halide.

In the example process shown for synthesis of an intermediate compound of formula XII, PG' is a more labile protective group than PG. This allows selective removal of PG' in the presence of PG. Examples of such pairs of protective groups would be: PG'=di-(p-methoxyphenyl)phenylmethyl; PG=triphenylmethyl or PG'=t-butyldimethylsilyl; PG=benzyl.

Scheme V
Intermediate Compound Synthesis
Intermediate Compounds of Formula V

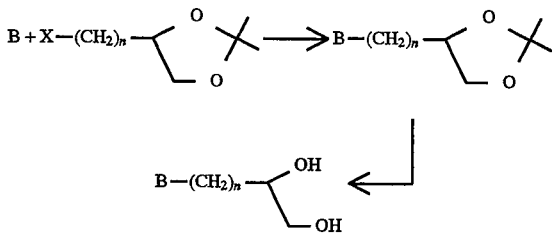

The process for preparing Formula V intermediates comprises a first step which is similar to that of Scheme I: generation of the base B anion and alkylation. The resulting alkylenyl acetonide derivative of the base is converted into the target intermediate V by standard acid cleavage of the acetonide moiety.

In summary, the general synthetic processes for preparation of compounds of Formula I comprise:

A. 1) alkylation of a purine or pyrimidine base anion with a leaving group derivative of a diesterified alkylenoxymethylphosphonate intermediate compound (II) to give the corresponding base derivative compound Ia;

2) conversion of Ia to either Ib by acid or base catalyzed hydrolysis or conversion to Ic by treatment of Ia with excess trimethylsilyl bromide, evaporation to dryness and treatment of the residue with water.

B. 1) protection of the reactive ring moiety of the base, e.g. the amino group of adenine or guanine, and a terminal hydroxy group of the starting diol compound V with synthetic organic protecting groups possessing the requisite steric and electronic characteristics appropriate for the necessary selectivity in bonding to give the di-protected intermediate IV;

2) converting the remaining hydroxy group to an oxy anion by treatment of IV with an alkali metal hydride followed by alkylation with a leaving group derivative of a diesterified methylphosphonate intermediate VI thereby giving intermediate III;

3) removal of the protecting groups from intermediate III to provide the phosphonate diester Ia; and 4) same processes as for A.2).

Physiologically acceptable salts of Formula I compounds of this invention are prepared by methods known in the art.

The salts include ammonium salts and salts of physiologically acceptable metals, particularly $Li^+$, $K^+$, $Na^+$, $Ca^{++}$ and $Mg^{++}$, and are novel compounds and comprise a further aspect of the invention. Metal salts can be prepared by reacting the metal hydroxide with a Formula 1 compound of this invention. Examples of metal salts which can be prepared in this way are salts containing $Li^+$, $Na^+$, and $K^+$. A less soluble metal salt can be precipitated from the solution of a more soluble salt by addition of the suitable metal compound. Acid salts may be prepared by reacting a Formula I compound of the invention with an inorganic or organic acid, e.g. HCl, HBr, $H_2SO_4$, and organic sulfonic acids, and the like.

The compounds of this invention, including the physiologically acceptable salts thereof, have desirable antiviral and antitumor activity. They exhibit activity against DNA viruses, for example, Herpes Simplex virus I, Herpes Simplex virus II, cytomegalovirus, Varicella Zoster virus and also against retroviruses. They are active against murine leukemia P388 and other experimental tumors. PMEG, the compound of Example 7 exerts a significant antitumor effect against murine leukemia P388 at a dose of 1 mg/kg i.p., and is comparable to olivomycin A in maximal antitumor effect.

For use against viral infections and against tumors, the compounds of this invention can be formulated into pharmaceutical preparations. Such preparations are composed of one or more of the Formula I compounds in association with a pharmaceutically acceptable carrier. The reference *Remington's Pharmaceutical Sciences*, 15th Edition by E. W. Martin (Mark Publishing Company, 1975) discloses typical carriers and methods of preparation.

For antiviral purposes, the compounds may be administered topically or systemically. For antitumor use, systemic, and preferably, parenteral administration is employed. By systemic administration is intended, oral, rectal, and parenteral (i.e. intramuscular, intravenous, subcutaneous and nasal) routes. Generally, it will be found that when a compound of the present invention is administered orally, a larger quantity of the reactive agent is required to produce the same effect as the smaller quantity given parenterally. In accordance with good clinical practice, it is preferred to administer the instant compounds at a concentration level that will produce effective antiviral or antitumor effect without causing any harmful or untoward side effects.

Therapeutically and prophylactically the instant compounds are given as pharmaceutical compositions comprised of an effective antiviral or antitumor amount of a compound of Formula I or a pharmaceutically acceptable salt thereof and a pharmaceutically acceptable carrier, as stated hereinabove. Pharmaceutical compositions for effecting such treatment will contain a major or minor amount, e.g. from 95 to 0.5% of at least one compound of the present invention in combination with a pharmaceutical carrier, the carrier comprising one or more solid, semi-solid, or liquid diluents, fillers, and formulation adjuvants which are non-toxic, inert and pharmaceutically acceptable. Such pharmaceutical compositions are preferable in dosage unit form; i.e. physically discreet units containing a predetermined amount of the drug corresponding to a fraction or multiple of the dose which is calculated to produce the desired therapeutic response. Other therapeutic agents can also be present. Pharmaceutical compositions providing form about 1 to 50 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents. (e.g. syrup, acacia, gelatin, sorbitol, tragacanth or polyvinylpyrrolidone), fillers (e.g. lactose, sugar, maize-starch, clacium phosphate, sorbitol, or glycine), lubricants (e.g. magnesium sterate, talc, polyethylene glycol or silica), disintegrants (e.g. starch) and wetting agents (e.g. sodium lauryl sulfate). Solutions or suspensions of a Formula 1 compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycol or mixtures thereof. The polyethylene glycols consist of a mixture of non-volatile, usually liquid, polyethylene glycols which are soluble in both water and organic liquids and have molecular weights from about 200 to 1500.

Considering the biological activities possessed by the compounds of the instant series, it can be seen that these compounds have antitumor and antiviral properties particularly suited to their use in combating viral infections or tumors. Thus, another aspect of the instant invention concerns a process for treating viral infections or tumors in a mammal in need of such treatment which comprises systemic or topical administration to such mammal of an effective dose of a Formula I compound or a pharmaceutically acceptable salt thereof. On the basis of testing, an effective dose could be expected to be from about 0.01 to about 30 mg/kg body weight with about 1 to about 20 mg/kg body weight a preferred dosage range. It is envisioned that for clinical antiviral application compounds of the instant invention will be administered in the same manner as for the reference drug acyclovir. For clinical applications, however, the dosage and dosage regimen must in each case be carefully adjusted, utilizing sound professional judgment and consideration of the age, weight and condition of the recipient, the root of administration and the nature and gravity of the illness. Generally a daily oral dose will comprise from about 150 to about 750 mg, preferable 250–500 mg of a Formula I compound administered from one to three times a day. In some instances, a sufficient therapeutic effect can be obtained at lower doses while in others, larger doses will be required.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees C when not specified. The nuclear magnetic resonance (NMR) spectral characteristics refer to chemical shifts (δ) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), triplet (t), or quartet (q). Abbreviations employed are DMSO-$d_6$ (perdeuterodimethylsulfoxide), CDCl$_3$ (deuterochloroform) and are otherwise conventional. The infrared (IR) spectral descriptions include only absorption wave numbers (cm$^{-1}$) having functional group identification value The IR determinations were employed using potassium bromide (KBr) as diluent. All compounds gave satisfactory elemental analyses.

I. Synthesis of Intermediates

A. Formula V Compounds

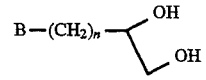

EXAMPLE 1

9-(S)-(2,3-Dihydroxy)propylguanine

A 250 mL 3-necked round bottomed flask fitted with a gas inlet, was oven dried, flushed with argon, and charged with sodium hydride (1.82 gm, 0.045 mol, 60% by weight in oil). The sodium hydride was washed twice with 50 mL of dry pentane (CaH$_2$), once with dry THF (Na/benzophenone), and covered with dry dimethylformamide (250 mL, distilled from P$_2$O$_5$). 2-Amino-6-benzyloxypurine (10.00 gm, 0.041 mol, prepared from 2-aminopurin-6-yl-trimethylammonium chloride) was added in one batch, axed the solution heated at 60° for 1 h. Isopropylidene-D-glycerol-γ-tosylate (11.86 gm, 0.041 mol, Fluka) was then added in one batch, followed by a catalytic amount (1 gm) of sodium iodide, and the resulting mixture heated for 12 h at 60°. The solution was then cooled and the volatiles removed under reduced pressure. Thin layer chromatographic analysis of the crude mixture revealed the presence of the N-9 isomer (Rf 0.7 in 10% methanol/methylene chloride) and the N-7 isomer (Rf 0.3 in same). Chromatography over silica gel eluting with ethyl acetate gave 10 gm of the N-9 isomer as a gum, and 2 gm of the crystalline N-7 isomer, mp. 184°–186° (80% overall yield, 5:1 ratio of N-9/N-7).

A solution of (S)-2', 3'-O-isopropylidene-6-O-benzyl-9-(2,3-dihydroxy)propylguanine (5.0 gm, 0.0139 mol) in 80% aqueous acetic acid (80 mL) was heated on a steam bath for 1 h. The volatiles were then removed in vacuo, and from the residue remaining were evaporated four 100 mL volumes of absolute ethanol followed by two 100 mL volumes of toluene. The white solid material obtained was recrystallized from water and dried at 5 mm for 12 h. to yield 2.8 gm (89%) of 9-(S)-(2,3-dihydroxy)propylguanine as a white solid, mp. above 260°.

$^1$H NMR (360 MHz,DMSO-$d_6$) δ10.57(s,1H), 7.58 (s,1H), 6.44(brs, 2H), 5.05(d, J=5 Hz, 1H), 4.77(t, J=5 Hz, 1H), 4.07(d, J=11 Hz, 1H), 3.77 (2 overlapping m, complex 2H), 3.35(m,complex, 1H), 3.27(m,complex, 1H); $^{13}$C NMR (90 MHz,DMSO-$d_6$) 156.90, 153.47, 151.32, 138.36, 116.38, 69.77, 63.51, 46.10; UV (0.1N aq. HCl) λmax 253(ε=12,305), λmax 272(ε=8.495); 0.1N aq. NaOH) λmax 256(ε=10,096), λmax 267 (ε=10,614; $[\alpha]_D^{25}$=–45 degrees, $[\alpha]_{456}^{25}$=–54 degrees (c=0.5, DMSO); IR(KBr) 3180 (br,s), 3100(s), 1695, 1650, 1605 cm$^{-1}$;

Analysis. Calculated for C$_8$H$_{11}$N$_5$O$_3$: C,42.66; H,4.92; N,31.09. Found: C,42.42; H,4.91; N,30.40.

B. Formula XII Compounds

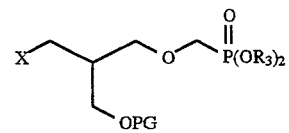

EXAMPLE 2

2-Benzyloxymethyl-3-diethylphosphonomethoxy-1-(p-toluenesulfonyloxy)propane

A solution of 5-hydroxymethyl-2,2-dimethyl-1,3-dioxane (cf:Bates, H. A.; Farina, J.; Tong, M. J. Org. Chem. 1986, 51, 2637, 3.0 g, 20.5 mmol) in 25 mL of dry DME under argon was added via cannula to a slurry of NaH (0.740 g, 80% dispersion in oil, 24.6 mmol) in 60 mL of dry DME cooled to 0° C. The resulting grey slurry was stirred at room temperature for 0.5 h, then recooled to 0° C., and treated with a solution of benzylbromide (4.56 g, 26.7 mmol) in 20 mL of DME. The reaction mixture was stirred at room temperature (rt) overnight and then quenched with 100 ml of $H_2O$. The aqueous layer was separated and extracted with two portions of ethyl acetate. The combined organic layers were then washed with saturated sodium chloride solution, dried over $MgSO_4$, filtered, and concentrated to provide a yellow oil. Purification by column chromatography on silica gel (ethyl acetate/hexane) afforded 3.51 g (72%) of 5-benzyloxymethyl-2,2-dimethyl-1,3-dioxane as a clear colorless liquid.

A mixture of 5-benzyloxymethyl-2,2-dimethyl-1,3-dioxane (3.40 g, 14.4 mmol) and a few crystals of p-toluenesulfonic acid monohydrate in 100 mL of methanol was stirred at room temperature for 20 h. The methanol was removed in vacuo and the residual oil purified by column chromatography on silica gel (ethyl acetate) to give 2.25 g (80%) of 2-benzyloxymethyl-1,3-propanediol as a colorless, clear liquid.

NaH (0.87 g, 80% dispersion in oil, 29.1 mmol) was washed three times with dry pentane, dried in vacuo, and then suspended in 60 mL of dry THF. A solution of 2-benzyloxymethyl-1,3-propanediol (5.70 g, 29.1 mmol) in 5 mL of THF was next added dropwise over 20 min. and the reaction mixture stirred at room temperature for 1.5 hrs. to give a white slurry. t-Butyldimethylsilylchloride (4.38 g, 29.1 mmol) was then added portionwise over 3 min. and the reaction mixture stirred at room temperature for 2 hours further. The mixture was next diluted with 150 mL of ethyl acetate and washed with 10% aqueous potassium carbonate and brine, dried over $MgSO_4$, filtered, and concentrated to give a colorless oil. Purification by column chromatography on silica gel (ethyl acetate/hexanes) provided 7.41 g (82%) of 2-benzyloxymethyl-3-t-butyldimethylsiloxy-1-propanol as a clear, colorless liquid.

A solution of 2-benzyloxymethyl-3-t-butyldimethylsiloxy-1-propanol (5.05 g, 16.3 mmol) in 10 mL of dry THF was added dropwise over 10 minutes to a slurry of NaH (0.59 g, 80% dispersion in oil, 24.4 mmol) in 70 mL of dry THF at 0° C. under argon. Upon completion of the addition, the ice-bath was removed and the reaction mixture stirred for 45 minutes at room temperature. A solution of diethyl phosphonomethyl-trifluoromethane sulfonate (Kluge, A. F. Org. Synthesis 1985 64, 80; Phillion, D. P; Andrew, S. S. Tetrahedron Lett. 1986, 27, 1477; 5.85 g, 19.5 mmol) in 10 mL of dry THF was then added over 5 minutes. After 3 hours at room temperature, the reaction mixture was heated at 50° C. for 2 hours and then cooled to room temperature. The reaction was next quenched by addition of 50 mL $H_2O$, diluted with $CH_2Cl_2$, and washed with $H_2O$ and saturated sodium chloride solution, dried over $MgSO_4$, filtered, and concentrated. The crude oil was purified by column chromatography on silica gel (EtOH/EtOAc) to provide 2.55 g of 2-benzyloxymethyl-1-t-butyldimethylsiloxy-3-(diethylphosphonomethoxy)propane as a colorless oil. $^1H$ NMR indicates that the compound is 80% pure. The major contaminant is unreacted diethyl phosphonomethyl triflate.

Tetrabutylammonium fluoride (8.3 mL, 1M in THF, 8.3 mmol) was added dropwise to a solution of 2-benzyloxymethyl- 1-t-butyldimethylsiloxy-3-(diethylphosphonomethoxy) propane (2.55 g, 5.5 mmol) in 20 mL of THF at room temperature. The reaction mixture was stirred at room temperature for 1.5 hours and then concentrated in vacuo to give 5.6 g of a yellow oil. Purification by column chromatography on silica gel (3–5% ethanol in ethyl acetate) provided 1.72 g (31% from 2-benzyloxymethyl-3-t-butyldimethylsiloxy-1-propanol) of 2-benzyloxymethyl-3-diethylphosphonomethoxy-1-propanol as a clear colorless oil.

A solution of 2-benzyloxymethyl-3-diethylphosphonomethoxy-1-propanol (0.25 g, 0.72 mmol) in 5 mL of $CH_2Cl_2$ was cooled to 0° C. and treated with triethylamine (0.22 g, 2.16 mmol). A solution of p-toluenesulfonyl chloride (0.151 g, 0.79 mmol) in 2 mL of $CH_2Cl_2$ was added next and the reaction mixture allowed to warm gradually to room temperature. After 14 hours at room temperature, the mixture was diluted with $CH_2Cl_2$ and washed with two portions of 10% aqueous HCl and saturated sodium chloride solution, dried over $MgSO_4$, filtered, and concentrated to give an orange oil. Purification by column chromatography on silica gel (1–3% ethanol in ethyl acetate) provided 0.295 g of 2-benzyloxymethyl-3-diethylphosphonomethoxy-1-(p-toluenesulfonyloxy) propane as a pale yellow oil.

$^1H$ NMR (200MHz,$CDCl_3$): 7.79(d, J=8.4 Hz, 2H), 7.21–7.39(m,7H),4.41 (brs,2H), 4.06–4.21 (m,6H), 3.71 (d, J=9 Hz,2H), 3.60(AB quartet, 2H), 3.48 (AB quartet, 2H), 2.44 (brs,3H), 2.31 (septet, J=5.8 Hz,1H) and 1.32 (t, J=7Hz,6H).

$^{13}C$ NMR (50 MHz,$CDCl_3$): 144.7, 137.9 g, 132.9, 129.8, 127.9, 127.6, 127.4, 73.2, 70.9 and 70.7, 68.3, 67.2, 67.1 and 63.8, 62.5 and 62.3, 39.7, 21.7, and 16.6 and 16.5.

IR(film): 3100, 3080, 3040, 3000, 2920, 2880, 1600, 1500, 1480, 1460, 1395, 1360, 1260, 1200, 1180, 1100, 1060, 1040, 980, 840, 820, 800, 750, 710, and 680 $cm^{-1}$.

C. Formula II Compounds

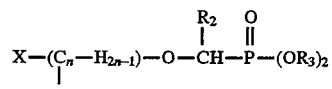

wherein

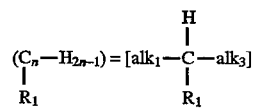

EXAMPLE 3

1-Methanesulfonyloxy-2-(diethylphosphonomethoxy)ethane

A solution of acetyl chloride (43.2 g, 550 mmol) in 100 mL of dry ether was added dropwise over 1 hour to a solution of 1,3 dioxolane (37.1 g, 500 mmol) in 300 mL of ether containing a few crystals of zinc (II) chloride at room temperature under nitrogen. The reaction mixture was stirred at room temperature for an additional 2 hours and then concentrated in vacuo. The product was purified by distillation (0.6 mmHg, 56°–58° C.) to provide 67.9 g (89%) of 1-acetoxy-2-(chloromethoxy)ethane as a clear colorless oil. cf: Foye, W. O.; Kaufmann, J. M.; Kim, Y. H. J. Heterocyclic Chem. 1987, 19, 497.

A mixture of 1-acetoxy-2-(chloromethoxy)ethane (67.8 g, 444 mmol) and triethylphosphite (81.3 g, 490 mmol) was heated at 105°–110° C. for 12 hours. Vigorous gas evolution was noted initially. The reaction mixture was next cooled to room temperature and the crude material purified by distillation (0.9 mmHg, 130°–134° C.) to afford 76.9 g (68%) of 1-acetoxy-2-(diethylphosphonomethoxy)ethane as a colorless liquid.

15 mL of concentrated hydrochloric acid was added in one portion to a solution of 1-acetoxy-2-(diethylphosphonomethoxy)ethane (76.5 g, 300 mmol) in 600 mL of absolute ethanol and the resulting mixture was heated at 55° C. for 12 hours. The reaction mixture was then cooled to room temperature and concentrated in vacuo. The resulting clear liquid could be used without purification or purified by distillation (1.5 mmHg, 128°–132° C.) to give 52.1 g (82%) of 2-diethylphosphonomethoxy-1-ethanol.

A solution of 2-diethylphosphonomethoxy-1-ethanol (40.7 g, 192 mmol) in 500 mL of $CH_2Cl_2$ was cooled to 0° C. and then triethylamine (29.1 g, 288 mmol) was added in one portion, followed by addition of methanesulfonyl chloride (26.4 g, 230 mmol) dropwise over 20 min. The reaction mixture was kept at 0° C. for 0.5 hours and then poured into water. The aqueous phase was extracted with two portions of $CH_2Cl_2$ and the combined organic phases dried over $MgSO_4$, filtered and concentrated to afford 54.4 g (98%) of 1-methanesulfonyloxy-2-(diethylphosphonomethoxy) ethane as a clear, pale orange oil. The mesylate could be employed without purification or purified by column chromatography on silica gel (5% methanol in $CH_2Cl_2$). 1H NMR (200 MHz, $CDCl_3$): 4.46–4.50 (m,2H), 4.26 (quintet, J=6.8 Hz,4H), 3.92–3.99(m,4H), 3.20 (s,3H), and 1.40 (t, J=7 Hz, 6H).

EXAMPLE 4

1-Bromo-4-(diethylphosphonomethoxy)butane

To a stirred solution of 49.5 g (323 mmol) of 1-bromo-4-butanol and 27.8 mL of 37% formaldehyde at 0° is slowly added anhydrous hydrogen chloride gas. The temperature is maintained at −5° to 0° during the slow 6 hour addition. The reaction mixture was then diluted wish 500 mL of $Et_2O$ and washed with 2×200 mL of ice water. The organic solution was dried ($MgSO_4$) and evaporated. The residue was distilled (55°–60°/0.2 mm) to obtain 29 g (45%) of 1-bromo-4-(chloromethoxy)butane as a colorless oil.

$^1$H NMR ($CDCl_3$) δ5.51 (s,2H), 3.71 (t,2H), 3.49(t,2H), 1.98(m,2H), 1.80(m,2H).

To a slurry of 6.26 g (149 mmol) of 57% NaH and 300 mL of n-pentane at 0° C. was added 17.14 g (124 mmol) of diethylphosphite and the mixture was stirred for 1 hour at 0°. The mixture was then cooled to −70° and 25 g (124 mmol) of 1-bromo-4-(chloromethoxy)butane was added and the reaction mixture warmed to 0° and stirred for 1 hour. The mixture was then filtered and evaporated. The residue was purified by $SiO_2$ chromatography to give 26 g (70%) of 1-bromo-4-(diethylphosphonomethoxy)butane as a colorless oil.

$^1$H NMR ($CDCl_3$) δ4.18 (m,4H), δ3.77 (d,2H), 3.61 (t,2H), 3.45 (t,2H), 1.95 (m,2H), 1.79 (m,2H), 1.35 (t,6H).

EXAMPLE 5

1-(Diethylphosphonomethoxy)-5-(methanesulfonyloxy)pentane

To a solution of 85.0 g (0.904 mole) of 1,5-pentanediol and 30.3 g (0.30 mole) of triethylamine in 350 mL of dry $CH_2Cl_2$ at −20° C. was added dropwise a solution of 28.5 g (0.25 mole) of methanesulfonylchloride in 100 mL of $CH_2Cl_2$ over 2 hours under nitrogen atmosphere. The solution was stirred at 2 hours at −20° C. and then at −4° C. for 18 hours. The reaction mixture was washed with $H_2O$, 1N HCl, $H_2O$, then dried and evaporated. The residual oil was chromatographed on a silica gel column, eluting with EtOAc-$CH_2Cl_2$ (2:8). After combining the appropriate fractions there was obtained 25.7 g (56.5%) of 5-hydroxypentylmethylsulfonate as a colorless oil.

$^1$H NMR ($CDCl_3$) 4.25 (t, J=6.2 Hz,2H), 3.65 (t, J=5.4 Hz,2H), 3.03 (s,3H), 2.35 (s,1H), and 1.75–1.85 (m,6H).

A mixture of 5-hydroxypentylmethylsulfonate (18.2 g 0.1 mole) and trioxane (3.6 g, 0.036 mole) in dichloroethane (30 mL) was saturated with dry HCl over a period of 2.5 hours with cooling (−10° C.). The resulting mixture was dried ($MgSO_4$) and filtered and the solvent evaporated in vacuo. A white oil (24 g) was obtained which could not be distilled in vacuo because of decomposition but was reacted as unpurified chloromethoxy intermediate.

$^1$H NMR ($CDCl_3$) 5.51 (s, 2H,), 4.28 (t, J=5 Hz, 2H), 3.68 (t, J=5.8 Hz,2H) 3.02 (s, 3H,) and 1.40 to 1.80 (m, 6H)

Sodium hydride (6.16 g, 0.154 mole as a 50% oil dispersion prewashed with n-pentane) was slurried in 100 mL n-pentane. The solution was cooled to 0° C. and a solution of 20.34 g (0.147 mole) diethylphosphite in 10 mL n-pentane was added dropwise over 20 mm. The slurry was cooled to −78° C. To this cold slurry was added a solution of the unpurified 5-chloromethoxy-1-methanesulfonoxypentane (31.0 g, 0.134 mole) in 120 mL THF with vigorous stirring. After the addition was completed the mixture was warmed to −15° in 2 to 3 hours. It was diluted with 500 mL ethyl acetate, washed with $H_2O$, dried over $MgSO_4$ and evaporated to dryness. The resulting oil was chromatographed through a silica gel column (10% EtOAc-$CH_2Cl_2$) to yield 22.5 g of a colorless oil (47%).

$^1$H NMR ($CDCl_3$) 4.3 (m, 6H), 3.8 (d, 2H), 3.6 (t, 2H), 3.0 (s, 3H), and 1.4–1.8 (m, 12H).

II. Synthesis of Products

EXAMPLE 6

9-(2-(Diethylphosphonomethoxy)ethyl)guanine(Ia)

A mixture of $N^2$-acetyl guanine (6.47 g, 33.5 mmol), 2-(diethylphosphonomethoxy)-1-iodoethane (9.80 g, 30.4 mmol) and potassium carbonate (8.41 g, 60.9 mmol) in 350 mL of dry DMF was heated at 100° C. for 4 h. The reaction mixture was then allowed to cool at rt and any insoluble material was removed by filtration. The filtrate was concentrated in vacuo to give a viscous yellow oil which was purified by column chromatography on silica gel (5–10% methanol in $CH_2Cl_2$). Recrystallization of combined fractions containing the desired product from ethyl acetate afforded a total of 1.50 g (13%) of 2-N-acetyl-9-(2'-(diethylphosphonomethoxy) ethylguanine as a white crystalline solid, m.p. 140.5°–141.5° C.

Analysis: Calculated for $C_{14}H_{22}N_5O_6P \cdot \frac{1}{2}H_2O$: C, 42.42%; H, 5.85%; N, 17.67%. Found: C, 42.33%; H, 5.60%; N, 17.99%.

2-N-Acetyl-9-(2-(diethylphosphonomethoxy)ethyl) guanine (1.42 g, 3.68 mmol) was dissolved in 50 mL of 40% aqueous methylamine and the solution was stirred at rt for 45 min. The reaction mixture was concentrated in vacuo and evaporated three times with toluene to give a gummy, white solid. The crude material was stirred in hot ethyl acetate for 1 h, then cooled to rt, and the product collected by filtration to provide 1.19 g of 9-(2-(diethylphosphonomethoxy)ethyl) guanine ¹H NMR (200 MHz,d₆-DMSO): 10.4–10.7(brs, 1H), 7.65 (s, 1H), 6.46 (brs, 2H), 4.14(t, J=7 Hz, 2H), 3.99(quintet, J=6 Hz, 4H), 3.78–3.89 (m, 4H), and 1.20 (t, J=7 Hz, 6H).

¹³CNMR(50.3MHz,d₆-DMSO): 156.7, 153.4, 151.1, 137.5, 116.3, 70.5 and 70.2, 65.4 and 62.2, 61.7 and 61.6, 42.1, and 16.2 and 16.1.

IR(KBr): 3200 (br), 3160, 3000, 1700, 1620, 1545, 1480, 1380, 1255, 1180, 1110, 1060, 1030, 900, 820, and 795 cm⁻¹.

Analysis. Calculated for $C_{12}H_{20}N_5O_5P\cdot\tfrac{1}{2}H_2O$: C, 40.68%; H, 5.98%; N, 19.77% Found: C, 40.61%; H, 5.74%; N, 19.79%.

EXAMPLE 7

9-(2-(Phosphonomethoxy)ethyl)guanine(Ic)

Bromotrimethylsilane (2.77 g, 18.1 mmol) was added dropwise over 2 min to a solution of 9-(2'-(diethylphosphonomethoxy)ethyl)guanine (0.625 g, 1.80 mmol) in 15 mL of dry DMF at rt under argon in a foil-covered flask. The reaction mixture was stirred at rt for 4 h and then volatiles were removed in vacuo to give a viscous yellow oil. The residue was treated with 5 mL of water, giving immediate formation of a white solid. 5 mL more water was added, followed by 10 mL of acetone; the precipitate was collected by filtration. The crude product was purified by recrystallization from water/ethanol to give 0.483 g of 9-(2-(phosphonomethoxy)ethyl)guanine as white crystals, m.p. >260°.

¹H NMR (200 MHz, d₆-DMSO): 10.55(brs, 1H, exch), 7.70(s, 1H), 6.45(brs, 2H, exch), 4.00–6.00(br m, exch), 4.12(t, J=7 Hz, 2H ), 3.80 (t, J=7 Hz, 2H), and 3.59(d, J=8.8 Hz, 2H).

¹³C NMR (50.3 MHz,d₆-DMSO): 157.0, 153.6, 151.3, 138.3, 116.1, 70.6 and 70.4, 68.0 and 64.8, and 42.6.

Analysis: Calculated for $C_8H_{12}N_5O_5P\cdot 2H_2O$: C, 29.54%; H, 4.96%; N, 21.54%. Found: C, 29.56%; H, 5.05%; N, 21.67%.

EXAMPLE 8

9- (2-(Monoethylphosphonomethoxy)ethyl)guanine (Ib)

9-(2-(diethylphosphonomethoxy)ethyl)guanine (0.198 g, 0.57 mmol) was dissolved in 15 mL of 1N sodium hydroxide solution and the mixture was stirred at room temperature for 1 hour. The solution was then acidified with 10% aqueous hydrochloric acid to pH 1 and concentrated in vacuo. Residual salts were removed by reverse phase column chromatography (C18 adsorbent, elution with water) to provide 0.150 g of 9-(2-(ethylphosphonomethoxy)ethyl) guanine as a white crystalline solid, mp=192.5°–193.5° C.

¹H NMR (200 MHz, d₆-DMSO): 10.6 (brs, 1H), 7.69 (s,1H), 6.48 (brs, 2H), 4.12 (t, J=5.2 Hz,2H), 3.89(quintet, J=7.2 Hz,2H), 3.81 (t, J=5.2 Hz,2H), 3.68 (d, J=8.6 Hz, 2H), and 1.15 (t, J=7.2 Hz, 3H).

EXAMPLE 9

9-(3-Hydroxy-2-(phosphonomethoxy)propyl) guanine(Ic)

A suspension of 9-(2,3-dihydroxy)propylguanine(5.0 g, 0.022 mol) in dry dimethylformamide was treated with 30 g (0.097 mol) p-anisyldiphenylchloromethane, 40 mL triethylamine, and 0.5 g N,N-dimethylaminopyridine, and the resulting mixture was heated for 12 h. at 80°. The solution was then cooled, methanol(50 mL) was added, and the volatiles were removed in vacuo at 70° and 5 mm. The residue was partitioned between ethyl acetate and water, and the combined ethyl acetate layers were dried (MgSO₄) and concentrated in vacuo. The dark oil remaining was chromatographed over silica gel eluting with 1:1 ethyl acetate/ hexanes to yield 4.5 g (27%) of the bis-monomethoxytrityl compound as a light orange foam, mp. 104°–106° (dec.).

A solution of the above bis-(monomethoxytrityl) compound (3.0 g, 0.0039 mol) in dry THF (30 mL) was treated in one batch with NaH (Aldrich, 0.311 g, 0.0041 mol, 60% by weight in oil). The solution was stirred for 15 minutes at room temperature, then treated with tosyloxymethyl diethylphosphonate (Holy, A.; Rosenberg, I. Collect. Czech. Chem. Commun. 1982, 47, 3447; 1.50 g, 0.0046 mol), and the resulting mixture stirred for 12 h. at room temperature. Thin layer chromatographic analysis of the crude mixture revealed the absence of the starting alcohol (Rf 0.4 in 1:1 ethyl acetate/hexanes) and presence of a single polar product (Rf 0.1 in same). Methanol (10 mL) was added and the volatiles were removed in vacuo. The oil remaining was dissolved in ethyl acetate, applied to a column of silica gel (ca. 3×300 cm) and eluted with pure ethyl acetate. The product was obtained in 40 fractions which were combined and concentrated in vacuo to yield 3.2 g 2-N-(monomethoxytrityl)-9-((2-diethylphosphonomethoxy)-3-(monomethoxytrityloxy)propyl)guanine (90%) of a colorless foam, mp. 78°–80°.

A solution of this bis-(monomethoxy)trityl diethyl phosphonate (1.5 gm, 0.0016 mol) in 80% aqueous acetic acid (50 mL) was heated gently on a steam bath for 0.5 h. Thin layer chromatographic analysis indicated that the starting phosphonate was absent, and that tritanol by-product and diethyl-HPMPG were the only compounds present. The solid material remaining after the trituration was dried by evaporating with toluene, and further dried in vacuo for two hours. The crude (Ia) product thus obtained (mp. 87–90 degrees) was treated with 5 mL bromotrimethylsilane in dry dimethylformamide (10 mL). The resulting light yellow mixture was allowed to stand at room temperature for 5 hours. The volatiles were then removed in vacuo, water (5 mL) followed by acetone (5 mL) was added, and the turbid solution kept at −20 degrees for 1 h. The solid that had formed was collected by suction filtration, washed with acetone, and recrystallized from water/acetone to yield 9-(3-hydroxy-2-(phosphonomethoxy)propyl)guanine as an off-white solid, mp. 185°–190° (dec.).

¹H NMR (360 MHz, DMSO-d₆) 7.72(s, 1H), 6.47(brs, 2H), 4.15(B part, ABq, J=3.5, 14 Hz, 1H), 3.98(A part, ABq, J=7, 14 Hz, 1H), 3.67(m, complex, 1H), 3.62(m, 5 lines, 2H), 3.37(m, complex, 2H), 3.37(m, complex, 2H); ¹³CNMR(90 MHz, DMSO-d₆ 156.72, 153.67, 151.31, 138.25, 115.83, 80.45 ($J_{C-O-C-P}$=10 Hz), 69.86, 66.39, 64.61 ($J_{C-P}$=160 Hz), 43.28.

EXAMPLE 10

8-Bromo-9-(2'-(phosphonomethoxy)ethyl)guanine (Ic)

Bromine (1 mL) was added to 100 mL of water and the mixture stirred vigorously at rt until all the bromine had dissolved (15 min.).

9-(2'-(diethylphosphonomethoxy)ethyl)guanine (0.360 g, 1.04 mmol) was then dissolved in 10 ml H₂O and treated dropwise with the aqueous bromine solution until the color of $Br_2$ persisted. The reaction mixture was allowed to stand at 0° C. for 1 h and then was concentrated to afford a dark yellow viscous gum. Purification was accomplished by column chromatography on silica gel (MeOH—$CH_2Cl_2$) to provide 0.31 g of 8-bromo-9-(2'-(diethylphosphonomethoxy)ethyl)guanine as an orange powder.

$^1$H NMR (200 MHz, $d_6$-DMSO): 6.58(brs, 2H), 4.12(t, J=5 Hz, 2H), 3.95(quintet, J=7 Hz,4H), 3.74–3.85(m, 4H), and 1.17(t, J=7Hz, 6H).

$^{13}$C NMR (50.3 MHz, $d_6$-DMSO): 155.4, 153.7, 152.4, 120.9, 116.6, 69.7 and 69.5, 65.7 and 62.5, 61.8 and 61.6, 43.1, and 16.2 and 16.1.

Bromotrimethylsilane (0.47 g, 3.1 mmol) was added dropwise over 5 min. to a solution of 8-bromo-9-(2'-(phosphonomethoxy)ethylguanine) (0.13 g, 0.31 mmol) in 3 mL of DMF at rt under argon in a foil-covered flask. The reaction mixture was stirred at rt for 4 h and then the solvent and excess silane were removed in vacuo. The resulting orange oil was treated with $H_2O$ and acetone to provide a fine pale yellow solid which was collected by filtration. The solid was purified by recrystallization from $H_2O$/EtOH to give 8-bromo-9-(2'-(phosphonomethoxy)ethyl) guanine as 21 mg of pale yellow crystals.

$^1$H NMR (200 MHz, $d_6$-DMSO): 10.6(brs, 1H), 6.63(brs, 2H), 4.10(t, J=5 Hz, 2H), 3.79(t, J=5 Hz, 2H), and 3.57(d, J=8 Hz, 2H).

$^{13}$C NMR (50.3 MHz, $d_6$-DMSO): 155.4, 153.8, 152.4, 120.8, 116.7, 69.3 and 69.2, 68.2 and 65.0, and 42.9.

EXAMPLE 11

9-(3-(Monoethylphosphonomethoxy)propyl)guanine (Ib)

A solution of 9-(3-diethylphosphonomethoxy)propyl-6-O-(methoxyethyl)guanine (Ia 417 mg, 1 mmol) in 10 mL of 3N HCl was heated at 85° for 3.5 hours. The solvent was removed using high vacuum to give 400 mg of the glassy monoester product.

$1_H$ NMR ($D_2O$) 7.95 (s, 1H), 4.38 (t, 2H), 4.15 (quintet, 2H), 3.85 (d, 2H), 3.70 (t, 2H), 2.25 (m, 2H), and 1.30 (T, 3H).

EXAMPLE 12

9-(4-(phosphonomethoxy)butyl)adenine (IC)

To a slurry of 0.962 g (22.8 mmol) of 57% NaH in 150 ml of distilled DMF was added in one portion 3.363 gm (24.9 mmol) of adenine. The mixture was heated at 80° for 1 hr. and then cooled to 30° and 6.30 g (20.7 mmol) of 4-(diethylphosphonomethoxy)-1-bromobutane was added and the mixture was warmed to 60° and stirred for 2 hrs. The solvent was then removed under high vacuum and the residue was triturated three times with 100 ml of $CH_2Cl_2$ and filtered. The combined filtrates were evaporated and purified by $SiO_2$ chromatography to give 4.9 g (66%) of Ia product as a white crystalline material mp 67°.

$^1$H NMR (CDCl$_3$) δ8.25(s, 1H), 7.80 (s, H), 6.50 (s,2H), 4.10 (m,6H), 3.67 (d,2H), 3.52 (t,2H), 1.91 (m,2H), 1.53 (m,2H), 1.23 (t,6H).

UV λmax (MeOH) 261 mm (ε14155)

Analysis: Calculated for $C_{14}H_{24}N_5O_4P$: C, 47.02; H, 6.77; N, 19.60. Found: C, 46.81; H, 6.83; N, 19.69.

To a solution of 3.3 g (9.2 mmol) of the Ia product in 75 mL of distilled DMF was added 13 mL (90 mmol) of bromotrimethylsilane. The solution was stirred at 20° for 5 hrs. and then concentrated in vacuo. The residue was crystallized from 30 mL $H_2O$ to give 2.5 g (90%) of Ic product as a white crystalline material, mp 238° C.

$^1$H NMR ($D_2O$) δ8.02 (s, 1H), 8.00 (s, 1H), 4.13 (t,2H), 3.66 (m,4H), 1.84 (m,2H), 1.67 (m,2H)

UV λmax (MeOH) 261 (ε13824)

Analysis: Calculated for $C_{10}H_{14}N_5O_4P$: C,39.87; H, 5.35; N, 23.25. Found: C,39.46; H,5.08; N,23.17.

EXAMPLE 13

9-(4-(phosphonomethoxy)butylguanine (Ic)

To a slurry of 560 mg (70 mmol) of LiH in 200 ml of distilled DMF was added B.0 g (41 mmol) of 6-O-(methoxyethyl)guanine. (Kjellberg, J.; Liljenberg, M.; Johannson, N. G. Tetrahedron Lett. 1986, 27, 877.) The mixture was stirred at 20° C. for 1.5 hrs. and then 12.6 g (41.5 mmol) of 4-(diethylphosphonomethoxy)-1-bromobutane in 5 ml of DMF was added and the mixture was heated at 60° C. for 4.5 hrs. The reaction mixture was then cooled to 10° C. and treated dropwise with dilute HCl to pH8. The solvents were then removed under high vacuum and the crude residue was purified by $SiO_2$ chromatography to give 4.2 g of the 0-6-protected Ia guanine product as a light yellow oil.

$^1$H NMR (CDCl$_3$) δ7.65 (s,1H), 4.92 (s,2H), 4.66 (t,2H), 4.15 (m,6H), 3.81 (m,4H), 3.62 (t,2H), 3.45 (s,3H), 1.96 (m,2H), 1.62 (m,2H), 1.35 (t,6H).

A solution of 3.0 gm (7.0 mmol) of Ia intermediate 6-O-(methoxyethyl)-9-(4-diethylphosphonomethoxy)butyl) guanine in 30 mL of 6N HCl was refluxed for 5.5 hrs. The solvent was then removed under high vacuum and the glassy residue was dissolved in 3 mL of $H_2O$ and diluted with acetone until cloudy. After stirring overnight 1.6 gm (73%) of crystalline Ic product was obtained, mp 240°.

$^1$H NMR ($D_2O$) δ7.813 (s,1H), 4.07 (t, 2H), 3.59 (m, 4H), 1.89 (m, 2H), 1.61 (m,2H).

UV max ($H_2O$) 271 ε=8494

Analysis: Calculated for $C_{10}H_{16}N_5O_5P$: C, 37.85; H, 5.08; N,22.07. Found: C,38.26; H,5.00; N,21.45.

EXAMPLE 14

1-(4-(phosphonomethoxy)butyl)thymine (Ia)

To a slurry of 0.634 g (15 mmol) 57% NaH in 80 ml of distilled DMF was added in one portion 2.07 g(16.4 mmol) of thymine. The mixture was heated at 80° for 1 hour. The reaction mixture was then cooled to 60° C. and to it was added 4.15 g (13.7 mmol) of 4-diethylphosphonomethoxy) -1-bromobutane and the mixture was warmed to 90° for 1 hour. The solvent was then removed under high vacuum, the residue was triturated with 3×100 mL $CH_2Cl_2$ and the fractions were combined and filtered. The residue was purified by $SiO_2$ chromatography to give 2.2 g (46%) of IA product as a colorless oil.

$^1$H NMR (CDCl$_3$) δ7.01 (s,1H), 4.07 (m,4H) 3.52 (t,2H), 1.82 (s,3H) 1.69 (m,2H) 1.55 (m,2H), 1.25 (t,6H).

To a solution of 2.0 g (5.75 mmol) of the diethyl phosphonate (IA) in 50 mL of distilled DMF was added 7.6 mL of bromotrimethylsilane. The solution was stirred 16 hours at 20° C. and the solvents were then removed under high vacuum. The glassy residue was crystallized from $H_2O$-acetone to Give 810 mg (48%) of white crystalline IC product mp 140°.

¹H NMR (D₂O) δ7.46 (s,1H), 3.73 (t,2H), 3.64 (d,2H) 3.58 (t,2H), 1.82 (s,3H), 1.69 (m,2H), 1.56 (m,2H).

By utilization of the foregoing examples which can be appropriately modified to produce the intermediate or product structure sought, such modifications being obvious to one skilled in the art; other examples of compounds embraced by the present invention can be prepared. As can be seen, the monoester compounds Ib and diacid compounds Ic are obtained readily from the diester precursors Ia. Additional examples of Formula Ib and Ic compounds which are prepared by the methods disclosed herein are shown in Tables 1, 2 and 3. The corresponding Ia analogs are intended to be understood as well.

TABLE 1

$$\text{B—alk}_1\text{—}\underset{\underset{Q}{|}}{\overset{\overset{R_1}{|}}{C}}\text{—alk}_3\text{—O—}\underset{\underset{OH}{|}}{\overset{\overset{R_2}{|}}{CH}}\text{—}\overset{\overset{O}{\|}}{P}\text{—OH} \qquad Ic$$
$$\overset{|}{\underset{|}{\text{alk}_2}}$$

| EX | B[a] | Alk₁[b] | Alk₂ | Alk₃ | O | R₁ | R₂ | MP (°C.) |
|---|---|---|---|---|---|---|---|---|
| 15 | G | — | — | CH₂ | H | Me | H | 210 (dec) |
| 16 | A | C₂H₄ | CH₂ | — | OH | H | H | |
| 17 | G | C₂H₄ | CH₂ | — | OH | H | H | |
| 18 | A | CH₂ | CH₂ | CH₂ | OH | H | H | 261.5–262.5 |
| 19 | G | CH₂ | CH₂ | CH₂ | OH | H | H | 246.5–247.5 |
| 20 | A | — | — | — | H | H | H | |
| 21 | G | — | — | — | H | H | H | |
| 22[c] | G | CH₂ | — | CH₂ | H | H | H | 280–285* |
| 23 | G | C₂H₄ | — | CH₂ | H | H | H | 240 (dec) |
| 24 | A | C₂H₄ | — | C₂H₄ | H | H | H | 236–238 |
| 25 | G | C₂H₄ | — | C₂H₄ | H | H | H | 174–177 |
| 26 | A | C₃H₆ | — | C₂H₄ | H | H | H | 225–230 (dec) |
| 27 | G | C₃H₆ | — | C₂H₄ | H | H | H | 240 (dec) |
| 28 | A | C₄H₈ | — | C₂H₄ | H | H | H | 238 (dec) |
| 29 | G | C₄H₈ | — | C₂H₄ | H | H | H | 228 (dec) |
| 30 | A | CH₂ | — | — | H | H | Me | |
| 31 | G | CH₂ | — | — | H | H | Me | >260 |
| 32 | G | CH₂ | — | — | H | Me | H | |
| 33 | C | CH₂ | — | — | H | H | H | 177–179 (softens) 222–224 (melts) |
| 34 | 2-Amino-purine | CH₂ | — | — | H | H | H | 258–260 |
| 35 | G | CH₂ | CH₂ | — | H | H | H | |
| 36[c] | C | CH₂ | CH₂ | — | OH | H | H | |

[a] G = guanine, A = adenine, T = thymine, C = cytosine, U = uracil.
[b] — = a chemical bond.
[c] The procedure is more fully described below with characterization data.

Procedure For Example 22

9-[3-(Phosphonylmethoxy)propyl]guanine

To a suspension of lithium hydride (560 mg, 60 mmol) in dry dimethylformamide (DMF, 200 ml) was added 2-amino-6-methoxyethoxy purine (8.0 g, 40 mmol) (prepared according to the literature procedure: J. Kjellberg, M. Liljenberg and N. G. Johansson, Tetrahedron Lett. 877, 1986]and stirred for 60 min at 25° C. To this solution was added over 3 min a solution of 3-(diethylphosphonomethoxy)-1-bromopropane (12.0 g, 41.5 mmol) in DMF (5 mL) and the solution was heated at 55° C. for 4 h. The reaction mixture was then cooled to room temperature and water (50 mL) was added dropwise. Insoluble material was removed by filtration. The filtrate was concentrated in vacuo to give a viscous oil which was purified by column chromatography on silica gel (5% methanol in CH₂Cl₂) to afford 2-amino-9-(3-(diethylphosphonomethoxy)propyl]-6-methoxyethoxy purine as a white crystalline solid: yield 3.45 g (21%); mp 78°–79° C.

Analysis: Calc. for C₁₆Hz₈N₅O₆P; C, 46.04; H. 6.76; M. 16.78 Found: C, 45.59; H, 6.75; N, 16.49

¹³C-NMR (50.3 MH3, d6-DMSO): δ113.73, 140.99, 152.99, 159.43, 160.43.

¹H-NMR (200 MHH3 d6-DMSO): δ1.34 (t, J=6.0 Hz, 6H), 2.12 (m, 2H), 3.52 (s, 3H), 3.62 (t, J=5.6 Hz, 2H), 3.80 (t, J=5.0 Hz, 2H), 3.88 (d, J=9.0 Hz, 2H), 4.02 (q, J-6.5 Hz, 4M), 4.16 (t, J=6.0 Hz, 2H), 4.57 (t, J=6.6 Hz, 2H), 5.0 (broad S, 2H), 7.83 (s, 1H).

A solution of 2-amino-9-(3-(diethylphosphonomethoxy) propyl]-6-methoxyethoxy purine (1.4 g, 3.4 mmol) in 3N HCl (10 mL) was heated at 85° C. for 4 h. The reaction was cooled to room temperature and concentrated in vacuo to give a viscous oil which was dissolved in DMF (5 mL). To this solution was added bromotrimethylsilane (5 mL) at 0° C. and the mixture was stirred at room temperature for 4 h under argon. The reaction was concentrated in vacuo to give a viscous yellow oil. The residue was dissolved in aqueous saturated NaHCO₃ (5 mL). The solution was then lyophilized to give a light yellow solid which was purified by the C-18 reverse phase column chromatography, eluting with water under 8 psi pressure. The fractions having ultraviolet absorption were collected and lyophilized to give the 9-[3-(phosphonomethoxy)propyl]guanine disodium salt as a white amorphous powder: yield 1.0 g (85%); mp 285°–300° C.

Analysis: Calc. for C₉H₁₂N₅O₅PNa₂H₂): C, 29.59; H, 3.86; N, 19.18. Found: C, 29.40; H, 4.24: N, 19.11

UV (H₂O): _max 269 nm (ε=9,525), 253 nm (ε=12,778)

¹H-NMR (200 MH₃, D₂O): δ2.09 (m, 2H), 3.57 (t, J=5.6 Hz, 2H), 3.61 (d, J=8.0 Hz, 2H), 4.17 (t, J=6.6 Hz, 2H), 7.84 (s, 1H).

Procedure for Example 36

S-N'-(3-Hydroxy-2-phosphonylmethoxy) propylcytosine

3-O-Benzyl-D-glycerol. A mixture of 1,2-O-isopropylidene-D-glycerol (150 g, 1.13 mol), benzyl bromide (350 g, 2.04 mol), benzyltriethylammonium bromide (7.5 g, 0.021 mol), and 450 mL of 10 N aqueous NaOH solution was stirred vigorously at 90°–95 ° C. for 15 h, then allowed to cool to room temperature, and poured into a two liter separatory funnel. The layers were separated and the aqueous phase was extracted with Et₂O (2×300 mL). The combined organic phases were washed with water (3×300 mL) and saturated NaCl solution (1×400 mL), dried over anhydrous Na₂SO₄, filtered, and concentrated to give a residual yellow oil. The residue was dissolved in 600 mL of 1.5 N aqueous H₂SO₄ solution and heated at 90° C. with vigorous stirring. After 5 h the reaction mixture was allowed to cool to room temperature and extracted with petroleum ether (bp 40°–60° C., 3×400 mL) to remove all dibenzyl ether, some benzyl alcohol, and only a small amount of the desired product. The aqueous phase was then adjusted to pH 10–12 by addition of 15% aqueous NaOH (600 mL); the solution became milky when basic pH was reached. The aqueous phase was extracted with ethyl acetate (3×500 mL) and the combined organic phases were washed with saturated NaCl solution (1×500 mL), dried over anhydrous Na₂SO₄, filtered, and concentrated to afford a yellow-orange oil. The product was purified by distillation to provide 169 g of 3-O-benzyl-D-glycerol (82% from 1,2-O- isopropylidene-D-glycerol) as a clear, pale yellow oil: bp 132°–135° C. (0.2 mm Hg); $[\alpha]_D^{20}$ −5.88° (neat) [lit. bp 140°–142° C. (0.15 mm Hg), $[\alpha]_D^{22}$ −5.85° (neat)]; IR (neat) 3200 (br, OH), 3180, 3100, 3000, 2960, 1615, 1518 (s), 1260 (s), and 980 cm$^{-1}$; $^1$H NMR (CDCl$_3$) δ7.33 (s, 5H, Ar H), 4.54 (s, 2H, benzylic), 3.82–3.90 (m, 1H, H-2), 3.50–3.65 (m, 4H, H-1 and H-3), 2.88 (d, J=4 Hz, 1H, C$_2$—OH), and 2.43 (br t, J=4 Hz, 1H, C$_1$—OH).

3-O-Benzyl-1-O-((p-methoxyphenyl)diphenyl)methyl-D-glycerol. 3-O-benzyl-D-glycerol (67.4 g, 0.370 mol) was dissolved in 600 mL of CH$_2$Cl$_2$ under argon and cooled to 0° C. (p-Methoxyphenyl)diphenylmethyl chloride (137 g, 0.444 mol) and dimethylaminopyridine (4.0 g, 0.032 mol) were added, and then triethylamine (75.0 g, 0.740 mol) was added dropwise via addition funnel over 20 min. A precipitate formed immediately upon addition of the amine. When the addition was complete, the ice-bath was removed and the resulting yellow-brown slurry was stirred at room temperature for 16 h and then was poured into water (600 mL). The layers were agitated and separated, and the aqueous phase was extracted with CH$_2$Cl$_2$ (500 mL). The combined organic layers were washed with 50% saturated NaHCO$_3$ solution (500 mL) and saturated NaCl solution (500 mL), dried over anhydrous Na$_2$SO$_4$, filtered, and concentrated to give 215 g of a yellow oil. The residue was coevaporated twice with toluene and used without purification. On a separate run (0.175 mol diol), the product was purified by chromatography on silica gel (5:1, 10% to 20% ethyl acetate/hexanes) to afford 75.5 g (90%) of 3-O-benzyl-1-O-((p-methoxyphenyl)diphenyl)methyl-D-glycerol as a viscous, pale yellow oil: $^1$H NMR (CDCl$_3$) δ7.45 (d, J=8 Hz, 2H, Ar H), 7.15–7.35 (m, 15H, Ar H), 6.82 (d, J=6 Hz, 2H, Ar H), 4.52 (s, 2H, benzylic), 3.90–4.14 (m, 1H, H-2), 3.77 (s, 3H, OCH$_3$), 3.50–3.62 (m, 2H, H-3), 3.15–3.28 (m, 2H, H-1), and 2.40 (d, J=4 Hz, 1H, OH); $^{13}$C NMR (CDCl$_3$) δ158.59, 144.36, 138.03, 135.49, 130.36, 128.82, 127.82, 127.67, 126.91, 113.12, 86.38, 73.36 (OCH$_2$Ph), 71.59 (C-2), 69.96 (C-3), 64.48 (C-1), and 55.20 (O-CH$_3$); mass spectrum (methane DCI), m/e (rel intensity) 454 (MH$^+$, 25), 377 (28), 273 (100).

3-O-Benzyl-2-O-(diethylphosphonyl)methyl-1-O-(p-methoxyphenyl)diphenylmethyl-D-glycerol. A solution of 3-O-benzyl-1-O-((p-methoxyphenyl)diphenyl)methyl-D-glycerol (215 g crude material),in 300 mL of THF was added dropwise via cannula over 25 min to a suspension of NaH (13.3 g, 80% dispersion in oil, 0.443 mol) in 400 mL of THF at room temperature under argon in a two-liter, three-necked, round-bottomed flask equipped with a reflux condenser. The resulting brown-grey slurry was stirred at room temperature for 30 min, and then was heated at reflux for 5 h to give a brown, cloudy solution. The reaction mixture was allowed to cool to room temperature, then was cooled to 0° C. with an ice-bath, and transferred via cannula over 30 min to a solution of diethyl tosyloxymethylphosphonate[9] 143 g, 0.443 mol) in 200 mL of THF cooled to 0° C. in a flask equipped with an overhead mechanical stirrer. Within 10 min, formation of a thick precipitate was observed; after 1 h, the ice-bath was removed, and the reaction mixture was stirred at room temperature for 14 h. The thick yellow-brown slurry was treated slowly with 100 mL of absolute EtOH and then concentrated in vacuo to near-dryness. The orange-brown residue was partitioned between ethyl acetate (600 mL) and water (600 mL), and the aqueous layer was extracted further with ethyl acetate (500 mL). The combined organic layers were washed with aqueous NH$_4$Cl solution (500 mL) and saturated NaCl solution (500 mL), dried over anhydrous Na$_2$SO$_4$, filtered, and concentrated to give 300 g of a viscous orange-brown oil. Purification by column chromatography on silica gel (5:1, 50% to 75% ethyl acetate/hexanes) gave 122 g of 3-O-benzyl-2-O-(diethylphosphonyl)methyl-1-O-(p-methoxyphenyl)diphenylmethyl -D-glycerol (55%) as a viscous pale yellow oil: IR (neat) 3000, 1600, 1370 (s), and 1180 cm$^{-1}$; $^1$H NMR (CDCl$_3$) δ7.45 (d, J=8 Hz, 2H, Ar H), 7.15–7.35 (m, 15H, Ar H), 6.80 (d, J=6 Hz, 2 H, Ar H), 4.50 (s, 2H, benzylic), 4.05–4.23 (m, 5H, H-2 and 2 POCH$_2$), 3.98 (d, J=8 Hz, 2H, OCH$_2$P), 3.77 (s, 3H, OCH$_3$), 3.55–3.65 (m, 2H, H-3), 3.22 (d, J=4 Hz, 2H, H-1), and 1.20–1.30 (m, 6H, 2 POCH$_2$CH$_3$); $^{13}$C NMR (CDCl$_3$) δ159.28, 145.04, 138.79, 136.12, 130.99, 129.03, 128.93, 128.57, 128.40, 128.14, 127.47, 113.63, 86.88, 81.17 (d, J=12 Hz, C-2), 73.71 (OCH$_2$Ph), 70.88 (C-3), 64.92 (d, J=165 Hz, OCH$_2$P), 63.61 (C-1), 62.82 (d, J=7 Hz, POCH$_2$), 55.52 (OCH$_3$), and 16.66 (d, J=6 Hz, POCH$_2$CH$_3$); mass spectrum (methane DCI), m/e (rel intensity) 604 (M+), 333, 301, 273 (100).

3-O-Benzyl-2-O-(diethylphosphonyl)methyl-D-glycerol. Procedure A. 3-O-benzyl-2-O-(diethylphosphonyl)methyl-1-O-(p-methoxyphenyl)diphenylmethyl-D-glycerol (42.0 g, 0.070 mol) was treated with 400 mL of 80% aqueous acetic acid and the mixture was placed on a steam bath for 20 min. The resulting bright yellow-orange solution was concentrated in vacuo and the yellow residue was coevaporated with 5% ethanol in toluene (2×200 mL) to give 45 g of a yellow oil. Purification by column chromatography on silica gel (10:1, 75% ethyl acetate/hexane to 8% ethanol/ethyl acetate) provided 19.9 g of the alcohol (86%) as a clear, colorless oil. Procedure B: A solution of 3-O-benzyl-2-O-(diethylphosphonyl)methyl-1-O-(p-methoxyphenyl)diphenylmethyl-D-glycerol (64.7 g, 0.107 mol) in 300 mL of methanol was treated with Amberlyst-15 ion-exchange resin (5.5 g, prewashed twice with 50 mL of methanol). The reaction mixture was stirred at room temperature for 16 h and then was filtered through a one-inch pad of Celite. The filtrate was concentrated in vacuo to give 63 g of a pale yellow oil which was purified by column chromatography as in Procedure A to provide 32.0 g of 3-O-benzyl-2-O-(diethylphosphonyl)methyl-D-glycerol (90%) as a clear, colorless oil: $[\alpha]_D^{20}$ −13.57° (c=1.57, CHCl$_3$); IR (neat) 3400 (s), 2960, 2920, 2860, 1240, 1100, 1050, 1030, and 980 cm$^{-1}$; $^1$H NMR (CDCl$_3$) δ7.28–7.40 (m, 5H, Ar H), 4.52 (s, 2H, benzylic), 4.03–4.24 (m, 5H, H-2 and 2 POCH$_2$), 3.85 (dd, J=5, 8 Hz, 1H, OCHP), 3.48–3.75 (m, 5H, H-1 and H-3 and OCHP), 3.23 (t, J=4 Hz, 1H, OH), 1.29 (t, J=6 Hz, 3H, POCH$_2$CH$_3$), and 1.27 (t, J=6 Hz, 3H, POCH$_2$CH$_3$); $^{13}$C NMR (CDCl$_3$) δ138.53, 129.02, 128.33, 128.22, 83.05 (d, J=9 Hz, C-2), 73.89 (OCH$_2$Ph), 70.62 (C-3), 64.99 (d, J=165 Hz, OCH$_2$P), 63.20 (d, J=6 Hz, POCH$_2$), 62.77 (C-1), and 16.61 (d, J=6 Hz, POCH$_2$CH$_3$); mass spectrum (methane DCI), m/e (rel intensity) 333 (MH$^+$, 100), 91 (10).

3-O-Benzyl-2-O-(diethylphosphonyl)methyl-1-O-methanesulfonyl-D-glycerol. A solution of 3-O-benzyl-2-O-(diethylphosphonyl)methyl-D-glycerol (32.0 g, 0.096 mol) in 350 mL of CH$_2$Cl$_2$ was cooled to 0° C. under argon. Methanesulfonyl chloride (13.2 g, 0.116 mol) was added rapidly via syringe, and after 10 min, triethylamine (19.5 g, 0.193 mol) was added dropwise via addition funnel over 15 min. The resulting pale yellow slurry was allowed to warm to room temperature over 16 h and then was poured into water (300 mL). The layers were agitated vigorously and separated, and the aqueous layer was back-extracted with CH$_2$Cl$_2$ (300 mL). The combined organic layers were washed with saturated NaHCO$_3$ solution (300 mL) and saturated NaCl solution (400 mL), dried over anhydrous MgSO$_4$, filtered, and concentrated to afford 39.9 g (101%) of crude mesylate as a yellow oil which was used without purification. On a separate run (0.089 mol alcohol), the mesylate was purified by column chromatography on silica gel (10:1, 75% ethyl acetate/hexane to 100% ethyl acetate) to afford 36.6 g (97%) of 3-O-benzyl-2-O-(diethylphosphonyl)methyl-1-O-methanesulfonyl-D-glycerol: $[\alpha]_D^{20}$ −10.87° (c=1.73, $CHCl_3$); IR (neat) 2960, 2940, 2920, 2860, 1360, 1250, 1180, 1100, 1050, 1030, 980, and 840 $cm^{-1}$; $^1H$ NMR ($CDCl_3$) δ7.25–7.38 (m, 5H, Ar H) 4.52 (s, 2H, benzylic), 4.38 (dd, J=5, 14 Hz, 1H, H-1), 4.25 (dd, J=8, 14 Hz, 1H, H-1), 4.13 (quintet, J=6 Hz, 2H, POC$\underline{H}_2$), 4.11 (quintet, J=6 Hz, 2H, POC$\underline{H}_2$), 3.82–3.96 (m, 3H, C-2 and OC$\underline{H}_2$P), 3.50–3.63 (m, 2H, H-3), 3.02 (s, 3H, OSO$_2$C$\underline{H}_3$), 1.28 (t, J=6 Hz, 3H, POCH$_2$C$\underline{H}_3$), and 1.27 (t, J=6 Hz, 3H, POCH$_2$C$\underline{H}_3$); $^{13}C$ NMR ($CDCl_3$) δ137.32, 128.34, 127.79, 127.59, 78.45 (d, J=11 Hz, C-2), 73.49 (O $\underline{C}H_2$Ph), 69.01 (C-3), 68.21 (C-1), 64.44 (d, J=165 Hz, O $\underline{C}H_2$P), 62.44 (d, J=6 Hz, PO$\underline{C}H_2$), 37.39 (OSO$_2\underline{C}H_3$), and 16.36 (d, J=5 Hz, POCH$_2\underline{C}H_3$); mass spectrum (methane DCI), m/e (rel intensity) 411 (MH$^+$, 100), 333 (5), 315 (20) and 91 (25). Anal ($C_{16}H_{27}O_8PS \cdot 0.25H_2O$) C, H.

(S)-$N^1$-(3-Benzyloxy-2-(diethylphosphonylmethoxy)propyl)cytosine. A solution of 3-O-benzyl-2-O-(diethylphosphonyl)methyl-1-O-methanesulfonyl-D-glycerol (10.0 g, 0.024 mol)in 50 mL of DMF was vigorously stirred and heated at 85°–90° C. in a 500 mL, three-necked, round-bottomed flask equipped with an overhead mechanical stirrer. Cytosine (3.25 g, 0.029 mol) was added in one portion followed by addition of cesium carbonate (15.9 g, 0.049 mol). The reaction mixture was stirred at 90° C. for 2.5 h, allowed to cool to room temperature, and then filtered to remove insoluble material. The filtrate was concentrated to give 15 g of a yellow oil. Purification by column chromatography on silica gel (15:1, 5% to 10% methanol/methylene chloride)provided 6.65 g (67%)of the desired N-alkylated product (S)-$N^1$-(3-benzyloxy-2-(diethylphosphonylmethoxy)propyl)cytosine along with 2.36 g (23%) of the O-alkylated isomer. For the N-alkylated isomer: UV$_{max}$ (MeOH) 274 nm (ε=7800); $^1H$ NMR (Me$_2$SO-$d_6$) δ7.40 (d, J=7 Hz, 1H, H-6), 7.25–7.40 (m, 5H, Ar H), 6.97 (br s, 2H, NH$_2$), 5.60 (d, J=7 Hz, 1H, H-5), 4.48 (s, 2H, benzylic), 3.70–4.08 (m, 8H, H-1', H-2', OC$\underline{H}$P, and 2 POC$\underline{H}_2$), 3.50–3.65 (m, 2H, OC$\underline{H}$P and H-3'), 3.44 (dd, J=5, 11 Hz, 1H, H-3'), and 1.10–1.25 (t, J=8 Hz, 6H, POCH$_2$C$\underline{H}_3$); $^{13}C$ NMR (Me$_2$SO-$d_6$) δ166.63 (C-4), 156.40 (C-2), 147.38 (C-6), 138.71, 128.69, 127.98, 127.90, 93.13 (C-5), 78.54 (d, J=11 Hz, C-2'), 72.69 (O$\underline{C}H_2$Ph), 69.47 (C-3'), 63.10 (d, J=165 Hz, O$\underline{C}H_2$P), 61.89 (d, J=6 Hz, PO $\underline{C}H_2$), 50.02 (C-1'), and 16.23 (d, J=5 Hz, POCH$_2\underline{C}H_3$); mass spectrum (methane DCI, m/e (rel intensity) 425 (M+). Anal. ($C_{19}H_{28}N_3O_6P \cdot 0.25 H_2O$) C,H,N. For the O-alkylated isomer: UV$_{max}$ (MeOH) 262 (ε=9100) 232 (ε=9400); $^1H$ NMR (Me$_2$SO-$d_6$) δ7.82 (d, J=7 Hz, 1H, H-6), 7.24–7.37 (m, 5H, Ar H), 6.82 (br s, 2H, NH$_2$), 6.07 (d, J=7 Hz, 1H, H-5), 4.50 (s, 2H, benzylic), 4.28 (dd, J=5, 14 Hz, 1H, H-1'), 4.19 (dd, J=8, 14 Hz, 1H, H-1'), 3.95–4.05 (m, 6H, H-2', OC $\underline{H}$P, and 2 POC$\underline{H}_2$), 3.85–3.95 (m, 1H, OC$\underline{H}$P), 3.53–3,65 (m, 2H, H-3'), and 1.18 (t, J=6 Hz, 6H, POCH$_2$C$\underline{H}_3$); $^{13}C$ NMR (Me$_2$SO-$d_6$) δ165.99 (C-4), 165.17·(C-2), 156.71 (C-6), 138.75, 128.67, 127.87, 99.88 (C-5), 78.82 (d, J=11 Hz, C-2'), 72.61 (O$\underline{C}H_2$Ph), 69.45 (C-3'), 65.50 (C-1'), 63.54 (d, J=160 Hz, O$\underline{C}H_2$P), 61.98 (d, J=6 Hz, PO$\underline{C}H_2$), and 16.26 (d, J=5 Hz, POCH$_2\underline{C}H_3$); MS: 425 (M+).

(S)-$N^1$-(3-Hydroxy-2-(diethylphosphonylmethoxy)propylcytosine. A mixture of (S)-$N^1$-(3-benzyloxy-2-(diethylphosphonylmethoxy)propyl)cytosine (12.5 g, 0.029 mol)and Pd(OH)$_2$ on carbon (12 g, 20%)in 160 mL of 1:1 ethanol/cyclohexene was heated at reflux. Thin layer chromatography showed no further progress in consumption of starting material after 4 h, so the reaction mixture was filtered through a 1-inch pad of Celite, and the collected solid was washed with hot EtOH. The filtrate was concentrated in vacuo and the pale yellow, glassy residue was dissolved in 160 mL of 1:1 ethanol/cyclohexene. Pd(OH)$_2$ on carbon (12 g, 20%) was added and the reaction mixture was heated at reflux for 8 h. The mixture was filtered while hot through a 1-inch pad of Celite, and the collected solid was rinsed with hot EtOH. The filtrate was concentrated in vacuo to give 9.8 g of a clear, pale yellow oil. Purification by column chromatography on silica gel (10:1, 7.5 to 10% methanol/methylene chloride) afforded 6.93 g (70%) of (S)-$N^1$-(3-hydroxy-2-(diethylphosphonylmethoxy)propylcytosine as a white foam, along with 0.49 g (5%) of the corresponding dihydrouracil overreduction product. For (S)-$N^1$-(3-hydroxy-2-(diethylphosphonylmethoxy)propylcytosine: UV$_{max}$(MeOH) 274 (ε=6800); $^1H$ NMR (Me$_2$SO-$d_6$) δ7.83 (br s, 1H, exch, NH), 7.50 (d, J=7 Hz, 1H, H-6), 7.34 (br s, 1H, exch, NH), 5.72 (d, J=7 Hz, 1H, H-5), 4.91 (br s, 1H, exch, OH), 3.88–4.02 (m, 6 H, H-1', H-2', 2 POC$\underline{H}_2$), 3.77 (dd, J=5, 14 Hz, 1H, H-1'), 3.53–3.64 (m, 2H, OC$\underline{H}_2$P), 3.36–3.47 (m, 2H, C-3'), 1.02 (t, J=6 Hz, 3H, POCH$_2$C$\underline{H}_3$), and 1.01 (t, J=6 Hz, 3H, POCH$_2$C$\underline{H}_3$); $^{13}C$ NMR (Me$_2$SO-$d_6$) δ165.83 (C-4), 155.89 (C-2), 147.04 (C-6), 92.96 (C-5), 80.08 (d, J=12 Hz, C-2'), 62.75 (d, J=170 Hz, O$\underline{C}H_2$P), 61.76 (d, J=6 Hz, PO$\underline{C}H_2$), 60.22 (C-3'), 49.43 (C-1'), and 16.30 (d, J=6 Hz, POCH$_2\underline{C}H_3$); mass spectrum (methane DCI), m/e (rel intensity) 336 (MH$^+$, 100), 318 (15), 290 (25). Anal. ($C_{12}H_{22}N_3O_6P \cdot H_2O$) C, H, N. For (S)-$N^1$-(3-hydroxy-2-(diethylphosphonylmethoxy)propyl-5,6-dihydrouracil: $^1H$ NMR (Me$_2$SO-$d_6$) δ8.16 (br s, 1H, exch, NH), 3.91–4.02 (m, 4H, 2 POC$\underline{H}_2$), 3.70 (d, J=8 Hz, 2H, OC$\underline{H}_2$P), 3.34–3.58 (m, 7H, OC$\underline{H}$P, H-6, H-1', H-2', H-3'), 2.47 (t, J=6 Hz, 2H, H-5), 2.03 (br s, 1H, exch, OH), 1.14 (t, J=6 Hz, 3H, POCH$_2$C$\underline{H}_3$), and 1.13 (t, J=6 Hz, 3H, POCH$_2$C$\underline{H}_3$); $^{13}C$ NMR (Me$_2$SO-$d_6$) δ169.89 (C-4), 153.35 (C-2), 81.43 (d, J=12 Hz, C-2'), 63.73 (d, J=165 Hz, O $\underline{C}H_2$P), 62.53 (d, J=6 Hz, PO$\underline{C}H_2$), 62.45 (d, J=6 Hz, PO $\underline{C}H_2$), 60.30 (C-3'), 47.91 (C-1'), 44.17 (C-6), 30.94 (C-5), and 16.30 (d, J=5 Hz, POCH$_2\underline{C}H_3$); mass spectrum (methane/DCI), m/e (rel intensity) 338 (MH$^+$, 100), 321 (20).

(S)-$N^1$-(3-Hydroxy-2-phosphonylmethoxy)propylcytosine. A solution of (S)-$N^1$-(3-hydroxy-2-(diethylphosphonylmethoxy)propylcytosine (9.20 g, 27.4 mmol) in 100 mL of anhydrous $CH_3CN$ was treated with bromo- trimethylsilane (42.0 g, 274 mmol) dropwise via syringe over 5 min at room temperature under argon. The resulting yellow solution was stirred at room temperature for 14 h and then the reaction mixture was concentrated in vacuo. The residual oil was placed under high vacuum (0.2 mm Hg) for 2 h and then was treated with water (20 mL). After 1 h, 200 mL of EtOH was added, and within 0.5 h a solid precipitated from the solution. The mixture was allowed to stand at 0° C. for 12 h, and then was filtered to provide 7.27 g (95%) of (S)-$N^1$-(3-hydroxy-2-phosphonylmethoxy)propylcytosine as a white powder. In order to remove trace amounts of EtOH, the solid was dissolved in 125 mL of hot water and the solution was lyophilized to give 7.30 g of (S)-$N^1$-(3-hydroxy-2-phosphonylmethoxy)propylcytosine as a fluffy, white solid: mp 260° C. (decomp); $[\alpha]_D^{20}$ −87.7° (c=1.052, H$_2$O); UV$_{max}$ (0.1N NaOH) 282 (ε=8800), (0.1N HCl) 274 (ε=5500); $^1H$ NMR (D$_2$O) δ7.85 (d, J=7 Hz, 1H, H-6), 6.13 (d, J=7 Hz, 1H, H-5), 4.15 (dd, J=3, 14 Hz, 1H, H-1'), 3.73–3.89 (m, 4H, H-1', H-2', and OC$\underline{H}_2$P), and 3.53–3.63

(m, 2H, H-3'); $^{13}$C NMR (D$_2$O) δ164.76 (C-4), 155.53 (C-2), 151.30 (C-6), 96.68 (C-5), 81.69 (d, J=11 Hz, C-2'), 68.15 (d, J=165 Hz, O$\underline{C}$H$_2$P), 62.10 (C-3'), and 52.15 (C-1'); mass spectrum (FAB), m/e (rel intensity) 279 (M$^+$, 100), 173 (85), 171 (90), 154 (20), 112 (40). Anal. (C$_8$H$_{14}$N$_3$O$_6$P·H$_2$O) C, H, N.

The sodium salt of HPMPC was prepared for in vivo studies. A solution of HPMPC (7.25 g, 24.4 mmol, monohydrate form) in 75 mL of water was treated with 1.00 N NaOH (41.0 mL, 41.0 mmol) until neutral pH was reached as indicated by a pH meter. The resulting solution was lyophilized to provide 8.29 g of the 1.7 sodium salt of HPMPC as a fluffy white powder: $^1$H NMR (D$_2$O) δ7.63 (d, J=7 Hz, 1H, H-6), 5.96 (d, J=7 Hz, 1H, H-5), 4.00 (dd, J=4, 14 Hz 1H, H-1') 3.65–3.83 (m, 4H, H-1', H-2', and OC$\underline{H}_2$P), and 3.46–3.59 (m, 2H, H-3'). Anal. (C$_8$H$_{12.3}$N$_3$O$_6$PNa$_{1.7}$·2.5 H$_2$O) C, H, N.

TABLE 2

Additional Compounds of Formula Ic

| EX | B | Alk$_1$ | Alk$_2$ | Alk$_3$ | O | R$_1$ | R$_2$ |
|---|---|---|---|---|---|---|---|
| 37 | 8-NH$_2$G | CH$_2$ | — | — | H | H | H |
| 38 | 8-MeG | CH$_2$ | — | — | H | H | H |
| 39 | T | CH$_2$ | — | — | H | Me | H |
| 40 | C | CH$_2$ | — | CH$_2$ | H | H | Me |
| 41 | U | CH$_2$ | CH$_2$ | — | OH | H | H |
| 42 | T | CH$_2$ | CH$_2$ | — | OH | H | H |
| 43 | T | CH$_2$ | — | — | H | H | H |
| 44 | U | CH$_2$ | — | — | H | H | Me |

G = guanine, T = thymine, C = cytosine, U = uracil.

The titer of HSV strains is determined by a plaque titration method (Roizman and Roane, "Virology," 15:75–79, 1961). Tissue culture 24-well petri dishes are seeded with cells and used for assays when approximately 75% monolayer. Volumes (0.1 ml) of logarithmic dilutions of the virus strain are inoculated onto each of triplicate wells, and absorbed for one hour with intermittent shaking. The inoculum thereafter is removed, and 1 ml of 5–10% EMEM containing 0.3% human immune serum globulin is added. After a 48 hr. incubation period at 37° C. in a 5% CO$_2$ atmosphere, the overlay medium is removed and the cell sheets stained with Giemsa stain. The number of plaques is counted, the triplicate is averaged, and the number of plaque-forming units per ml is calculated.

The compounds are tested for activity against the herpes simplex strains using a stock solution of each compound freshly prepared. Appropriate dilution of each compound are made in 10% EMEM before usage. The antiviral efficacy of each compound is determined using the plaque reduction assay described above. Briefly, tissue culture 24-well plates, with approximately 75% cell monolayer are inoculated with approximately 50 plaque forming units of HSV per 0.1 ml, and the virus adsorbed for, 1 hr, with intermittent shaking. After removal of the inoculum, 1 ml of 10% EMEM containing two-fold dilutions of the appropriate drug are added in triplicates. Triplicate wells/plate receives no drug and are used as a virus control. After a 48-hour incubation period, at 37° C. in a 5% CO$_2$ atmosphere, the overlay medium is removed, the cells stained as described above, and plaques are counted. The counts of triplicate wells are averaged, and the number of plaques In the presence of each drug dilution are calculated.

The antiviral potency of the drug is determined by ID$_{50}$, the drug concentration necessary to reduce the number of plaques by 50% of those in the virus control cultures.

TABLE 3

$$B-alk_1-\underset{\underset{Q}{\overset{|}{alk_2}}}{\overset{\overset{R_1}{|}}{C}}-alk_3-O-\overset{\overset{R_2}{|}}{\underset{\underset{OH}{|}}{CH}}-\overset{\overset{O}{\|}}{P}-OR^3 \quad Ib$$

| EX | B | Alk$_1$ | Alk$_2$ | Alk$_3$ | O | R$_1$ | R$_2$ | R$_3$ | MP (°C.) |
|---|---|---|---|---|---|---|---|---|---|
| 45 | G | CH$_2$ | — | — | H | H | H | CH$_3$ | 199 (dec) |
| 46 | G | CH$_2$ | — | — | H | H | H | CH$_2$CH$_2$CH$_3$ | 195–197 |
| 47 | G | CH$_2$ | — | — | H | H | H | CH(CH$_3$)$_2$ | 222.5–224 |
| 48 | G | CH$_2$ | — | — | H | H | Me | CH$_2$CH$_3$ | |
| 49 | 2-Aminopurine | CH$_2$ | — | — | H | H | H | CH$_2$CH$_3$ | |
| 50 | G | CH$_2$ | CH$_2$ | — | OH | H | H | CH$_2$CH$_3$ | |
| 51 | G | CH$_2$ | CH$_2$ | — | H | H | H | CH$_2$CH$_3$ | |
| 52 | C | CH$_2$ | CH$_2$ | — | OH | H | H | CH$_2$CH$_3$ | |
| 53 | G | — | — | CH$_2$ | H | Me | H | CH$_2$CH$_3$ | 80 (dec) |

G = guanine, C = cytosine

III. Biological Testing

EXAMPLE 54

Testing and evaluation of compounds against herpes virus.

A. Plaque Reduction Assay

Herpes simplex virus (HSV) strains were grown and titered at 37° C. in veto cells (African Green Monkey Kidney cells) and used for virus work before the tenth passage.

Cells were grown and maintained in Earle's Minimum Essential Medium (EMEM), Gibco Laboratories, supplemented with 0.75% sodium bicarbonate, 2 mM 1-glutamine, Pen-strep. and 5–10% fetal calf serum.

B. Colorimetric Dye-Uptake Assay

For the primary screening, a colorimetric dye-uptake assay (McLaren, C., et al., "Antiviral Research," 3:323, 1983) is used employing rapidly growing vero cells. Briefly, cells, compound and virus dilutions are added onto 96-well tissue culture plates simultaneously using the cells, viruses and medium described above. After 48 hr. incubation at 37° C. in 5% CO$_2$ atmosphere, the overlay medium is removed and the cell sheets are stained with 0.04% neutral red solution. After 30 min. incubation at 37° C. the cell sheets are washed and the stain is eluted with 0.05M sodium monophosphate in 47% ethanol and the O.D. is determined at 540 nm wave length.

The 50% inhibitory dose (ID50) for each drug is determined by linear regression analysis.

EXAMPLE 55

Testing and evaluating of compounds against human cytomegalovirus.

Human cytomegalovirus (HCMV) strain (AD169) was grown and titered at 37° in human embryonic lung (diploid) cells, MRC-5, and used for the antiviral assay.

The compounds are tested for activity against the HCMV using the procedure for the plaque reduction assay described above.

EXAMPLE 56

Testing and evaluating of compounds against Murine Retroviruses:

The compounds were evaluated for antiviral activity against Murine leukemia virus (MuLV) strains using the UV-XC plaque assay (Rowe, et al., "Virology," 42:1136, 1970).

The MuLV strains were grown in fetal mouse cells (SC-1) and used for antiviral tests using the UV-XC plaque assay. Briefly, SC-1 cells are grown as monolayers in 4-well tissue culture plates and inoculated with approximately 50–100 plaque forming units of MuLV in 0.5 ml of 5% EMEM containing 20 ug/ml DEAE/Dextran. After 1 hr. adsorbtion, the inoculum is removed and 5 ml of 5% EMEM containing three-fold dilutions of the appropriate drug are added. Five days later, the cultures are UV-irradiated with an ultraviolet lamp and rat XC sarcoma cells are added to the cultures. Three-four days after UV-irradiation, the cell cultures are stained with Giemsa stain and the plaques are enumerated. Antiviral activity is expressed in terms of the reduction in the mean number of UV-XC plaques counted in the drug treated, virus-infected cultures compared with mean number of plaques counted in untreated, virus-infected control cultures.

Some representative antiviral test data are displayed in Table 4.

TABLE 4

Antiviral Test Results of Some Representative Formula I Compounds

| Reference Cmpds. | Dye-Uptake | | Plaque Reduction | | | |
| --- | --- | --- | --- | --- | --- | --- |
| | HSV-1 | HSV-2 | HSV-1 | HSV-2 | CMV | Mulv |
| Acyclovir | 0.5 | 1.0 | 0.3 | 1.5 | | N.T. |
| 9-(1,3-Dihy-droxypropoxy-methyl)guanine | | | | | 1.2 | |
| 3'-Azido-3'-deoxy-thymidine | N.T. | N.T. | N.T. | N.T. | | 0.0003 |
| (S)-9-(3-Hydroxy-2-phosphonomethoxy)propyladenine Formula I Compounds | 15.1 | >25 | 13.8 | 35.8 | 0.13 | 2.0 |
| Ex. 7 | <0.6 | N.T. | 0.04 | 0.31 | 0.04 | <1 |
| Ex. 8 | 12 | 8 | 4.8 | 5.1 | 0.23 | 0.56 |
| Ex. 9 | 25 | 30.0 | 2.8 | 21.6 | 0.56 | 2.1 |
| Ex. 15 | 8.7 | 10.4 | 4.0 | 3.3 | | |
| Ex. 22 | >64 | >76 | | | 6.0 | 0.04 |
| Ex. 34 | | | | | >0.032 | |
| Ex. 45 | 1.5 | 3.8 | 1.6 | 1.2 | | 0.05 |
| Ex. 46 | | | 9.7 | 9.9 | | |
| Ex. 47 | | | 74.9 | 34.8 | | 1.72 |
| Ex. 13 | >104 | >113 | | | >10 | >32 |

TABLE 4-continued

Antiviral Test Results of Some Representative Formula I Compounds

| Reference Cmpds. | Dye-Uptake | | Plaque Reduction | | | |
| --- | --- | --- | --- | --- | --- | --- |
| | HSV-1 | HSV-2 | HSV-1 | HSV-2 | CMV | Mulv |
| Ex. 11 | >122 | >130 | | | 9.5 | 2.5 |
| Ex. 19 | | | 69 | 158 | | >32 |
| Ex. 18 | | | >143 | >106 | | >32 |
| Ex. 10 | >138 | >100 | | | | 1.66 |
| Ex. 31 | >113 | | | | 47 | 14 |
| Ex. 45 | | | 1.6 | 1.2 | | 0.05 |
| Ex. 47 | | | 74.9 | 34.8 | | 1.7 |
| Ex. 53 | 137 | >166 | | | | |
| Ex. 46 | | | 9.7 | 9.9 | | |
| Ex. 36 | | | 5.3 | 2.3 | 0.2 | |

EXAMPLE 57

Comparison of Example 36 Product (HPMPC) and Acyclovir (ACV) In Vivo

Groups of ten mice were inoculated intraperitoneally with from 200 to 600 PFU/0.2 ml of Herpes simplex virus-1 (HL-34 strain). Different doses of test compound were administered to separate groups of animals on a BID basis for five consecutive days commencing three hours after inoculation. Treatment was by intraperitoneal route. The experiment was terminated 21 days post inoculation and the number of survivals in each group was counted. The mean survival time (MST, days) was calculated. The results are shown in Table 5. HPMPC is approximately 100× as active as ACV.

TABLE 5

Murine Survival Times Post HSV-L Inoculation

| Dose (mg/kg/day) | Percent Surviving | | MST (days) | |
| --- | --- | --- | --- | --- |
| | HPMPC | ACV | HPMPC | ACV |
| 200 | 100 | 78 | 21.0 | 18.2 |
| 100 | 100 | 70 | 21.0 | 18.4 |
| 50 | no test | 50 | no test | 15.1 |
| 10 | 100 | 20 | 21.0 | 10.4 |
| 1 | 90 | no test | 19.7 | no test |
| 0.1 | 50 | no test | 14.9 | no test |

EXAMPLE 58

In Vivo Comparison of Various Other Compounds

This evaluation was carried out by the method described in Example 57 but this time Herpes simplex virus-2 (strain G) was employed. The results are reported in Table 6 in the same format used in Table 5. The compounds tested, are designated as follows:

| ACV | acyclovir |
| --- | --- |
| HPMPA | DeClerq et al., Nature (1986) 323, 464-7. |
| PMEA | DeClerq et al., Nature (1986) 323, 464-7. |
| PMEG | Example 7 |
| HPMPC | Example 36 |
| HPMPG | Example 9 |
| EPMG | Example 8 |

TABLE 6

Murine Survival Percent Post HSV-2 Inoculation

| Dose | ACV | HPMPA | PMEA | PMEG | HPMPC | HPMPG | EPMG |
|---|---|---|---|---|---|---|---|
| 200 | 80 | none | 30 |  | 100 |  |  |
| 100 | 23 | 10 | none |  | 100 |  | 92 |
| 50 | 40 | 30 | 20 |  |  | none | 100 |
| 25 | 20 |  |  |  |  |  | 96 |
| 12.5 |  |  |  |  |  |  | 42 |
| 10 | 11 |  |  | none | 100 | none |  |
| 6.25 |  |  |  |  |  |  | 50 |
| 5 |  |  |  | 92 |  |  |  |
| 3.13 |  |  |  |  |  |  | 17 |
| 1 |  |  |  | 100 | 60 | 80 |  |
| 0.25 |  |  |  | 90 |  |  |  |
| 0.125 |  |  |  | 60 |  |  |  |
| 0.10 |  |  |  |  |  | 40 | 10 |
| 0.05 |  |  |  |  |  |  | 40 |
| 0.03 |  |  |  | 20 |  |  |  |

The following conclusions can be drawn from Table 6. PMEG (Example 7) has exceptionally high potency against HSV-2 in mice since 100% survival was achieved at a dose of 1 mg/kg. Doses above 5 mg/kg were toxic but nevertheless the compound had a good therapeutic index in view of the high potency.

HPMPC (Example 36) also possesses very high potency but is much less toxic than PMEG or HPMPA (DeClerq, et al., Nature, 1986, 323, pp. 464–467).

HPMPG (Example 9) is another very potent compound comparable to PMEG.

EPMG (Example 8) is substantially more active than either ACV, HPMPA, or PMEA against HSV-2 infection in mice. It is highly efficacious as a topical agent in healing HSV-1 lesions in guinea pigs. It is more suitable for the latter purpose than PMEG (EPMG is the monoethylester of PMEG), since PMEG is irritating to the skin while EPMG is not irritating.

PMPG (Example 22) is active in vitro against human immunodeficiency virus having about 1/10 the potency of AZT and is comparable to the latter against mouse leukemia virus, a virus widely used to study retrovirus infections in vivo.

What is claimed is:

1. The compound of Formula I

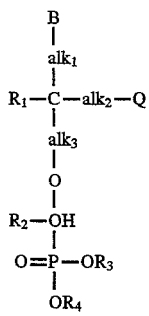

I wherein

B is a base selected from the group consisting of xanthine, hypoxanthine, 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine, and 2-amino-6-methoxyethoxypurine;

$alk_1$ is $C_{1-4}$ alkylene;

$alk_2$ is independently selected from a chemical bond and $C_{1-4}$ alkylene;

$alk_3$ is a chemical bond;

Q and $R_2$ are hydrogen;

$R_1$ is independently selected from hydrogen and $C_{1-4}$ alkyl and wherein one of $R_1$ or $alk_2$ are $C_{1-4}$ alkyl or $C_{1-4}$ alkylene respectively;

$R_3$ and $R_4$ are independently selected from hydrogen, $C_{1-6}$ alkyl, phenyl, and phenyl-$C_{1-4}$-alkylene;

and the corresponding salts, and solvates thereof; provided, however, that when B is 2-amino-6-methoxyethoxypurine then $R_3$ and $R_4$ are ethyl, $alk_2$ is a bond, $R_1$ is H and $alk_1$—C($R_1$)($alk_2$Q)-$alk_3$ is 1,3 propylene or 1,4 butylene.

2. The compound of claim 1 wherein the base is a purine base selected from the group consisting of 8-bromoguanine, 8-chloroguanine, 8-aminoguanine, 8-hydrazinoguanine, 8-hydroxyguanine, 8-methylguanine, 8-thioguanine, 2-aminopurine, 2,6-diaminopurine and 2-amino-6-methoxyethoxypurine.

3. The compound of claim 2 wherein $R_1$ is $CH_3$ and $alk_2$ is a bond.

4. The compound of claim 2 wherein $alk_2$ is $CH_2$ and $R_1$ is H.

5. The compound of claim 1 wherein at least one of $R_3$ or $R_4$ is not hydrogen.

6. The compound of claim 2 wherein at least one of $R_3$ or $R_4$ is not hydrogen.

7. The compound of claim 1 wherein at least one of $R_3$ or $R_4$ is phenyl or phenyl-$C_{1-4}$-alkylene.

8. The compound of claim 2 wherein at least one of $R_3$ or $R_4$ is phenyl or phenyl-$C_{1-4}$-alkylene.

9. The compound of claim 1, wherein $alk_1$ is methylene and $R_1$ is hydrogen.

10. The compound of claim 1, wherein $alk_1$ is methylene, $R_1$ is hydrogen and B is 2-aminopurine.

11. The compound of claim 1, wherein $alk_1$ is methylene, $R_1$ is hydrogen and B is 2,6-diaminopurine.

* * * * *